United States Patent
Chadha et al.

(10) Patent No.: US 9,760,680 B2
(45) Date of Patent: Sep. 12, 2017

(54) COMPUTERIZED SYSTEM AND METHOD OF GENERATING HEALTHCARE DATA KEYWORDS

(71) Applicant: Syntel, Inc., Troy, MI (US)

(72) Inventors: Ankur Chadha, Talawade Pune (IN); Sabari Mallika Ramakrishnan, Talawade Pune (IN); Sandeep Sinha, Talawade Pune (IN); Alok Srivastava, Talawade Pune (IN)

(73) Assignee: Syntel, Inc., Troy, MI (US)

( * ) Notice: Subject to any disclaimer, the term of this patent is extended or adjusted under 35 U.S.C. 154(b) by 301 days.

(21) Appl. No.: 14/222,031

(22) Filed: Mar. 21, 2014

(65) Prior Publication Data

US 2015/0269320 A1    Sep. 24, 2015

(51) Int. Cl.
*G06F 7/00* (2006.01)
*G06F 17/00* (2006.01)
*G06F 19/00* (2011.01)
*G06F 17/30* (2006.01)

(52) U.S. Cl.
CPC ...... *G06F 19/322* (2013.01); *G06F 17/30569* (2013.01)

(58) Field of Classification Search
CPC ............................ G06F 19/322; G06F 19/3487
USPC ........................................................ 707/690
See application file for complete search history.

(56) References Cited

U.S. PATENT DOCUMENTS

| | | | |
|---|---|---|---|
| 6,507,948 B1 * | 1/2003 | Curtis | G06F 8/30 717/174 |
| 6,516,312 B1 | 2/2003 | Kraft et al. | |
| 8,037,041 B2 | 10/2011 | Gupta | |
| 8,527,292 B1 * | 9/2013 | Ozden | G06Q 30/04 705/2 |
| 2002/0069376 A1 * | 6/2002 | Gregg | G06F 3/0619 714/6.12 |
| 2003/0041095 A1 * | 2/2003 | Konda | G06F 17/30569 709/201 |
| 2003/0083903 A1 * | 5/2003 | Myers | G06F 19/324 705/2 |
| 2004/0172297 A1 * | 9/2004 | Rao | G06F 19/328 705/2 |

(Continued)

OTHER PUBLICATIONS

Facets, "Provider Batch Import Subsystem User Guide" (Mar. 1999, 112 pgs.).

(Continued)

*Primary Examiner* — Binh V Ho
(74) *Attorney, Agent, or Firm* — Dykema Gossett PLLC

(57) ABSTRACT

A system, method, and computer program product for generating healthcare data keyword files is disclosed. The system may include a reader module on a computer, a mapper module on a computer, and a generator module on a computer. The reader module may be configured to read one or more healthcare data fields associated with a first vendor and read one or more portions of healthcare data associated with the one or more data fields. The mapper module may be configured to allow a first mapping of the one or more data fields to one or more keyword fields. In accordance with the first mapping, the generator module may be configured to generate one or more keywords associated with the one or more portions of healthcare data.

12 Claims, 32 Drawing Sheets

(56) References Cited

U.S. PATENT DOCUMENTS

| | | | |
|---|---|---|---|
| 2004/0249665 A1* | 12/2004 | David | G06Q 10/10 705/2 |
| 2004/0260577 A1* | 12/2004 | Dahlin | G06Q 50/22 705/2 |
| 2006/0129434 A1* | 6/2006 | Smitherman | G06F 19/322 705/3 |
| 2006/0259331 A1* | 11/2006 | Lurtz | G06Q 50/24 705/3 |
| 2007/0100659 A1* | 5/2007 | Preiss | G06Q 10/10 705/2 |
| 2008/0010087 A1* | 1/2008 | Daniel | G06Q 40/08 705/2 |
| 2008/0033750 A1* | 2/2008 | Burriss | G06F 19/328 705/2 |
| 2010/0088095 A1* | 4/2010 | John | G10L 15/22 704/235 |
| 2010/0293162 A1 | 11/2010 | Odland et al. | |
| 2011/0055099 A1* | 3/2011 | Paul | G06Q 10/00 705/321 |
| 2011/0077958 A1* | 3/2011 | Breitenstein | G06Q 10/10 705/2 |
| 2011/0282690 A1* | 11/2011 | Patel | G06Q 30/0603 705/3 |
| 2012/0215857 A1* | 8/2012 | Bohner | G06F 19/327 709/206 |
| 2012/0259754 A1* | 10/2012 | Ravisankar | G06Q 30/08 705/37 |
| 2013/0080414 A1* | 3/2013 | Dudala | G06F 17/30398 707/706 |
| 2013/0096938 A1* | 4/2013 | Stueckemann | G06F 19/34 705/2 |
| 2013/0311201 A1* | 11/2013 | Chatfield | G06F 19/3418 705/3 |
| 2014/0278506 A1* | 9/2014 | Rogers | G06F 19/3406 705/2 |
| 2014/0379364 A1* | 12/2014 | Liu | G06F 19/3487 705/2 |
| 2015/0302070 A1* | 10/2015 | Gross | G06F 17/30286 707/756 |

OTHER PUBLICATIONS

Facets, "Introduction to Facets" (1997, 82 pgs.)
Facets, "Membership Maintenance Subsystem User Guide" (Dec. 1998, 152 pgs.)
Trizetto, "The Trizetto Facets Core Administrative System" (2013, 8 pgs.)

* cited by examiner

901

3401

COMPUTERIZED SYSTEM AND METHOD OF GENERATING HEALTHCARE DATA KEYWORDS

TECHNICAL FIELD

This disclosure relates generally to a computerized system and method for managing healthcare-related data; and in particular, the disclosure relates to a system and method for generating healthcare-related data keywords for use by healthcare management software.

BACKGROUND

Healthcare services are often provided by large healthcare organizations or enterprises, such as hospitals, clinics, physician groups, and the like. In some cases, these enterprises are expansive, encompassing numerous doctors and facilities. Consequently, managing healthcare-related data, such as patient information and records, clinical information, financial information, insurance claims, and other data involved in the day-to-day business of healthcare enterprises can be extremely complex.

As such, many healthcare enterprises employ software to more efficiently and accurately perform the complex tasks healthcare management entails. However, existing healthcare management software may only accept data in a certain file format. Further, ensuring data is of the proper format, and, in some cases, mapping data to the proper file format (e.g., a keyword format) can be time consuming and require the use of many resources. Therefore, a need exists for a tool to convert healthcare data to a proper file format as input into healthcare management software.

SUMMARY

According to an aspect of the present disclosure, a system and method for generating healthcare data keyword files is disclosed. The system may include a reader module on a computer, a mapper module on a computer, and a generator module on a computer. The reader module may be configured to read one or more healthcare data fields associated with a first vendor and read one or more portions of healthcare data associated with the one or more data fields. The mapper module may be configured to allow a first mapping of the one or more data fields to one or more keyword fields. In accordance with the first mapping, the generator module may be configured to generate one or more keywords associated with the one or more portions of healthcare data.

In another aspect of the present disclosure, the reader module may be further configured to read one or more healthcare data fields associated with a second vendor. The mapper module is further configured to allow a second mapping associated with one or more healthcare data fields. The first vendor may be a healthcare provider and the second vendor may be a healthcare patient.

Additional features and advantages of the will become apparent to those skilled in the art upon consideration of the following detailed description of the illustrated embodiment exemplifying the best mode of carrying out the invention as presently perceived. It is intended that all such additional features and advantages be included within this description and be within the scope of the invention.

BRIEF DESCRIPTION OF THE DRAWINGS

The present disclosure will be described hereafter with reference to the attached drawings which are given as non-limiting examples only, in which.

Figure 1:
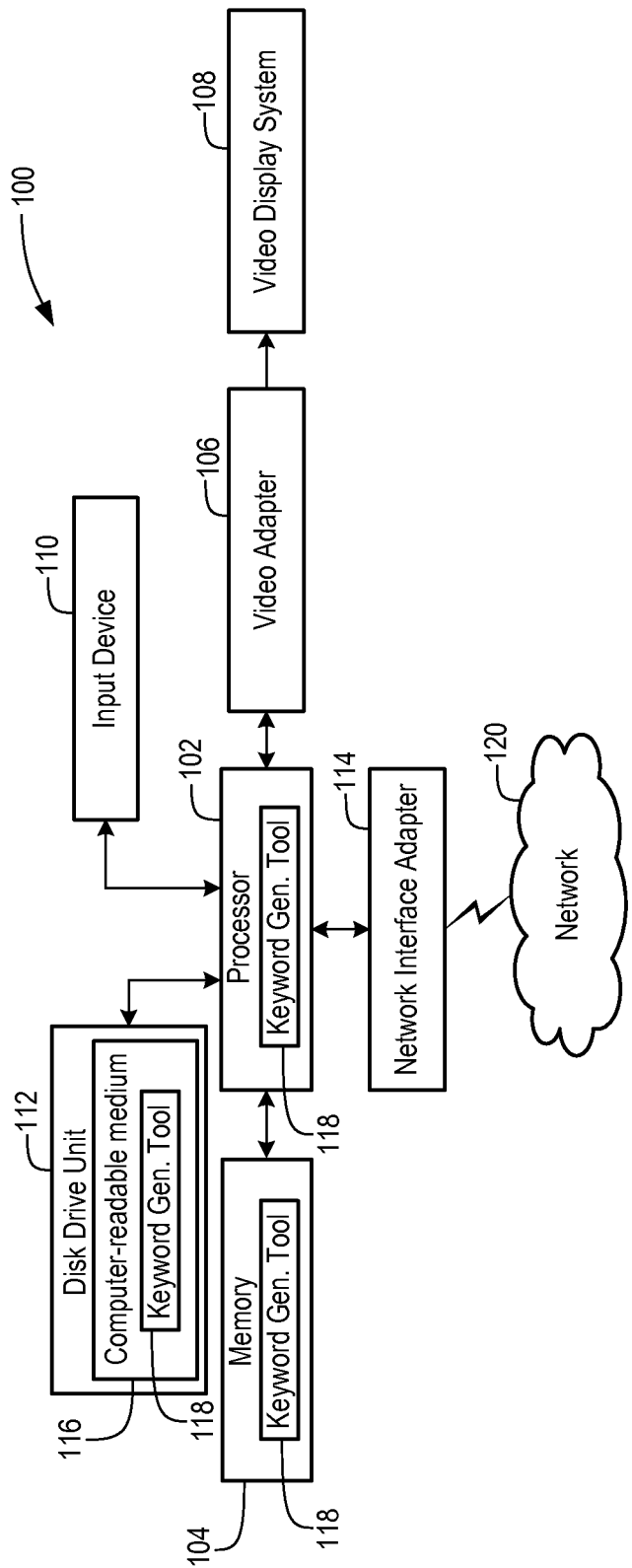
FIG. 1 is a diagrammatical view of an example computing device that may be included in the system and that may be programmed to carry out various methods taught herein according to an embodiment of the disclosure.

Corresponding reference characters indicate corresponding parts throughout the several views. The components in the figures are not necessarily to scale, emphasis instead being placed upon illustrating the principals of the invention. The exemplification set out herein illustrates embodiments of the invention, and such exemplification is not to be construed as limiting the scope of the invention in any manner.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the disclosure.

Embodiments of the present disclosure include a keyword generator tool for receiving inbound data (from an external system, for example) containing various types of healthcare information of one format, mapping this inbound data according to user configured mappings, and, based on these mappings, automatically generating data in a different format (e.g., a format defined by keywords) for compatibility with healthcare management software. The input data may include healthcare provider data and/or healthcare patient data. Healthcare provider data could include, but is not limited to healthcare provider names, addresses, network affiliations, and credentials. Healthcare patient data could include but is not limited to healthcare patient names, addresses, coordination of benefit (COB) data, and primary care physician (PCP) selections.

In some embodiments, healthcare management software may take of the form of Facets™ software, offered by TriZetto Corporation of Englewood, Colo. Accordingly, in such embodiments, the keyword generator tool can validate keyword values and generate valid batch files in a compatible Facets™ keyword file format. For example, the Facets™ Membership Maintenance Subsystem (MMS) is a batch load process that facilitates the initial loading and subsequent maintenance of healthcare subscriber and/or patient information. Likewise, the Facets™ Provider Import Subsystem (XP/F) is a batch load process that facilitates the initial loading and subsequent maintenance of healthcare provider information.

In some embodiments, the keyword file format is made up of two parts. One skilled in the art should appreciate that embodiments are contemplated with less or more than two parts for the file format. In this embodiment, the first part is the actual keyword which will be identified by the software to process the patient and/or provider data correctly. The first part, in this embodiment, ends with a literal (=) and is followed by the second part which is the actual data. An example of a keyword is: @pPRCP_LAST_NAME="Smith".

FIG. 1 illustrates a diagrammatic representation of a machine 100, in the example form of a computer system, that may be programmed with a set of instructions to perform any one or more of the methods discussed herein. The machine may be a personal computer, a notebook computer, a server, a tablet computer, a personal digital assistant ("PDA"), a cellular telephone, or any machine capable of executing a set of instructions (sequential or otherwise) that specify actions to be taken by that machine.

The machine 100 may operate as a standalone device or may be connected (e.g., networked) to other machines. In embodiments where the machine is a standalone device, the set of instructions could be a computer program stored locally on the device that, when executed, causes the device to perform one or more of the methods discussed herein. Consider an example in which the machine 100 is a tablet device, such as an iPad™ or Android™ device; the computer program could be an "app" installed on the tablet device. In embodiments where the computer program is locally stored, data may be retrieved from local storage or from a remote location via a network. In a networked deployment, the machine 100 may operate in the capacity of a server or a client machine in server-client network environment, or as a peer machine in a peer-to-peer (or distributed) network environment. Although only a single machine is illustrated in FIG. 1, the term "machine" shall also be taken to include any collection of machines that individually or jointly execute a set (or multiple sets) of instructions to perform any one or more of the methods discussed herein.

The example machine 100 illustrated in FIG. 1 includes a processor 102 (e.g., a central processing unit ("CPU")), a memory 104, a video adapter 106 that drives a video display system 108 (e.g., a liquid crystal display ("LCD") or a cathode ray tube ("CRT")), an input device 110 (e.g., a keyboard, mouse, touch screen display, etc.) for the user to interact with the program, a disk drive unit 112, and a network interface adapter 114. Note that various embodiments of the machine 100 will not always include all of these peripheral devices.

The disk drive unit 112 includes a computer-readable medium 116 on which is stored one or more sets of computer instructions and data structures embodying or utilized by a keyword generator tool 118 described herein. The computer instructions and data structures may also reside, completely or at least partially, within the memory 104 and/or within the processor 102 during execution thereof by the machine 100; accordingly, the memory 104 and the processor 102 also constitute computer-readable media. Embodiments are contemplated in which the keyword generator tool 118 may be transmitted or received over a network 120 via the network interface device 114 utilizing any one of a number of transfer protocols including but not limited to the hypertext transfer protocol ("HTTP") and file transfer protocol ("FTP").

The network 120 may be any type of communication scheme including but not limited to fiber optic, cellular, wired, and/or wireless communication capability in any of a plurality of protocols, such as TCP/IP, Ethernet, WAP, IEEE 802.11, or any other protocol.

While the computer-readable medium 116 shown in the example embodiment of FIG. 1 is a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing a set of instructions for execution by the machine and that cause the machine to perform any one or more of the methods described herein, or that is capable of storing data structures utilized by or associated with such a set of instructions. The term "computer-readable medium" shall accordingly be taken to include, but not be limited to, solid-state memories, optical media, flash memory, and magnetic media.

Figure 2:
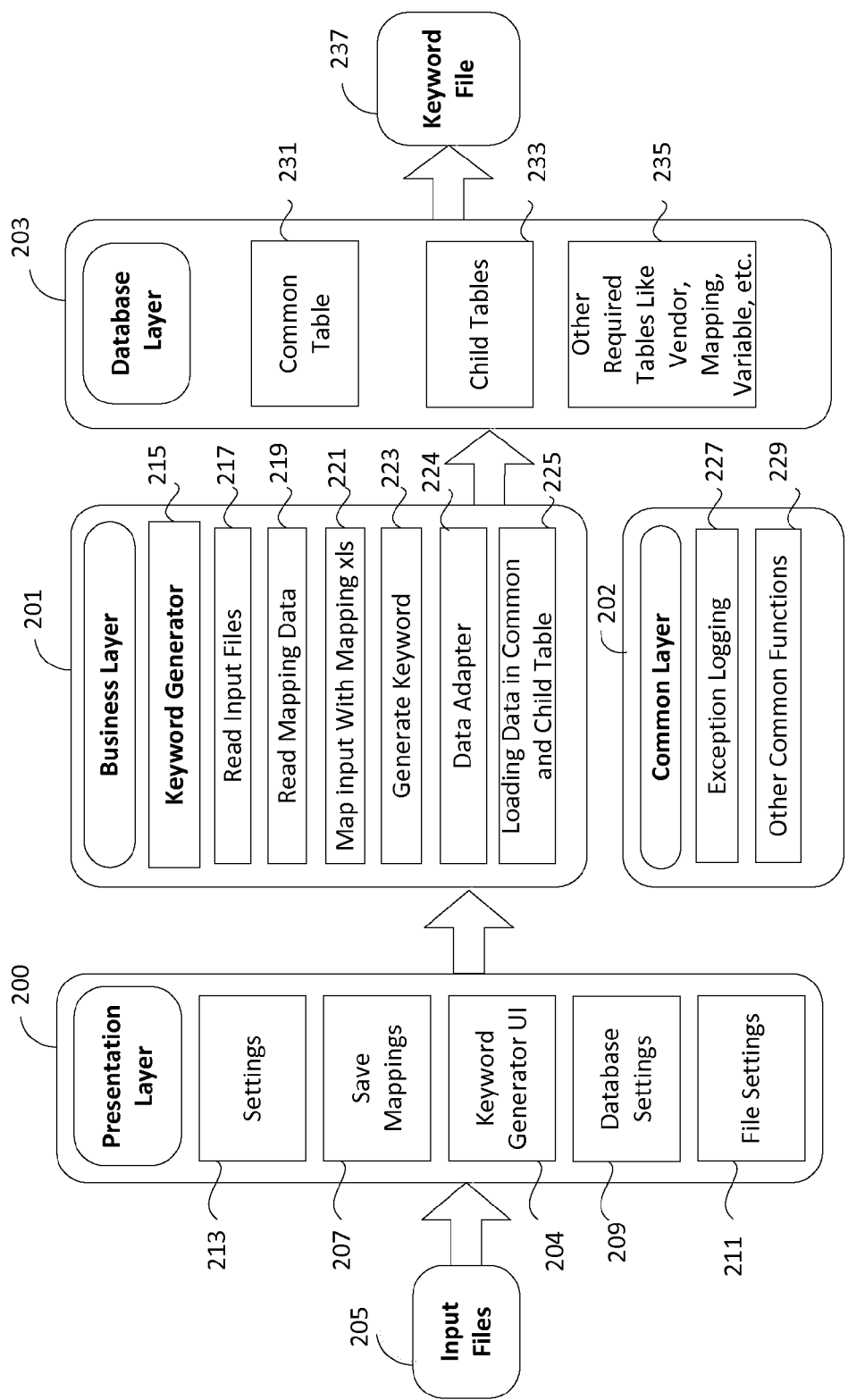
FIG. 2 is a block diagram of an example system architecture according to one embodiment of the disclosure.

FIG. 2 is a block diagram of an exemplary architecture of the keyword generator system. The architecture includes, but is not limited to: a presentation layer 200, a business layer 201, a common layer 202, and a database layer 203.

In the embodiment shown, the presentation layer 200 provides an interface 204 for a user to input data such as one or more input files 205, and performs validation of the input files 205. The presentation layer 200 can also read and save mappings 207, allow for the configuring and adjusting of database settings 209, file settings 211, and any general settings 213.

As shown, the business layer 201 includes a keyword generator component 215 responsible for the keyword generator functionality. The business layer 201 reads the input files 205 at block 217 and reads the mapping data at 219. The business layer 201 may then map the input files 205 with the mapping data at 221. From this mapped data, the business layer 201 may generate a keyword file 237 at 223. The business layer 201 may also detect whether or not there is proper interaction between the database layer 203 and the user interface 204. The data adapter 224 can analyze the data in the common table through application of business rules on the data. Moreover, the business layer 201 may load mapped data into common and child tables at 225. The common layer 202 includes components for performing exception handling and logging 227 as well as other common functions 229.

Figure 3:
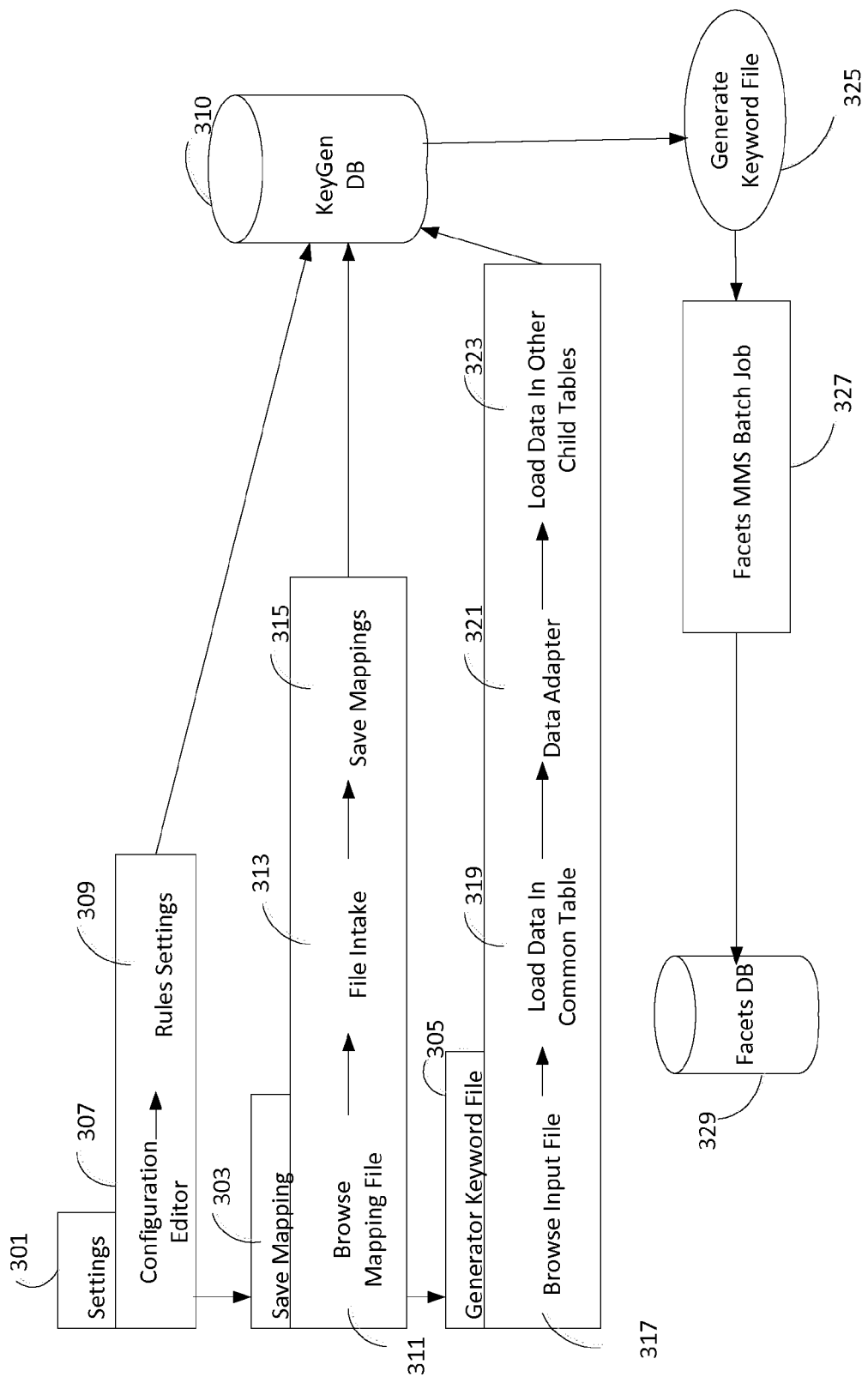
FIG. 3 is a system diagram according to one embodiment of the disclosure.

The database layer 203 interacts with any created table, including but not limited to:
- Common tables 231 used to load all data
- Child tables 233, which may be replicas of Facets™ tables depending on record types
- Other tables 235, including:
  - Vendor tables used to store vendor data
  - Mapping tables used to store mappings for various vendors Variable tables used to store all variables used in keyword generation In accordance with the foregoing, and as shown in FIG. 3, embodiments of the disclosure may include functionalities including, but not limited to settings 301, save mapping information 303, and keyword file generation 305. The settings functionality 301 involves setting initial level values in a configuration editor screen 307 and rules setting screen 309. These settings can be stored in a tool database 310. The configuration editor 307 can be used to set information about any platforms being used and database credentials. The rules settings 309 can be used to set different types of business rules, which may be customer specific.

The save mapping information functionality 303 includes, but is not limited to, the following tasks:
browsing of a mapping file 311
file intake 313
save mappings 315

The browse mapping file task 311 allows a user to browse the mapping file that has been provided by a customer. The mapping file may be vendor specific. The file intake task 313 allows a user to set file and field definitions. The save mappings task 315 allows for saving of the specific vendor mapping information in the tool database 310 against a particular vendor identification.

The keyword generation functionality 305 includes, but is not limited to, the following tasks:
browsing of an input file 317
loading data in a common table 319
data adapter 321
loading data in a child table 323

The browsing functionality 317 allows a user to browse an input file for a specified vendor. Once the file is browsed, through the common table data loading task 319, data can be loaded in one common table. The data adapter 321 can analyze the data in the common table through application of business rules on the data. Once the analysis is complete, the data from the common table may get loaded into child tables in a child table task 323 and stored in the tool database 310.

With these stored data including rules settings, mappings, and actual patient and provider healthcare input data, the tool can generate a keyword file at 325. This keyword file is then loaded as a batch job 327 for input into the healthcare management system (e.g., Facets) and stored in a respective database 329.

Figure 4:
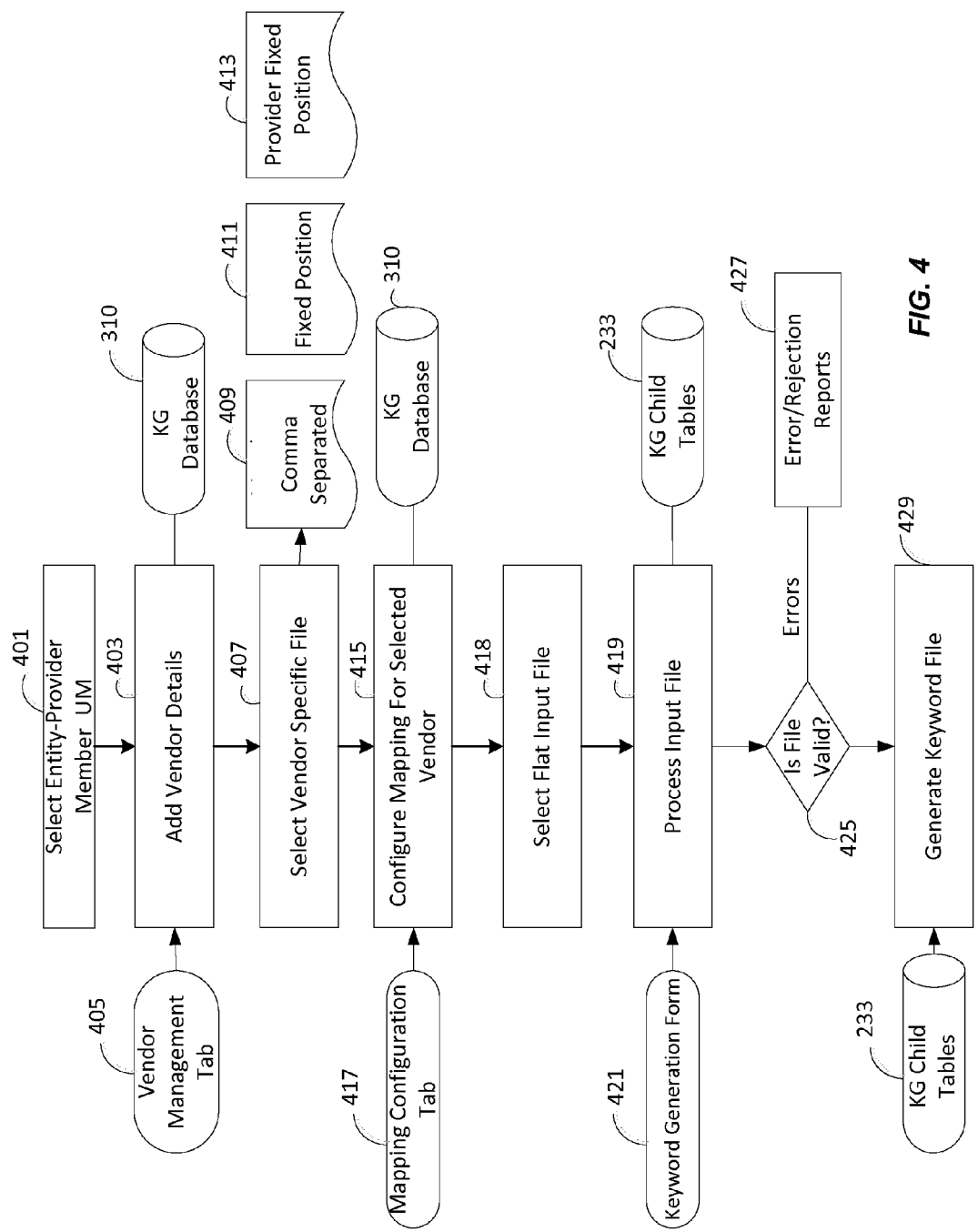
FIG. 4 is a flow diagram showing example steps that could be performed by the system according to an embodiment of the disclosure.

In light of the foregoing, embodiments of the disclosure may be illustrated as a flow diagram as shown in FIG. 4. At block 401, a user may select a type of vendor entity (e.g., healthcare provider, healthcare patient, and the like). At block 403, via the vendor management tab 405, the user may add details pertaining to the vendor entity. For example, the user may add specific vendor names, specific fields, and the like. These details may be stored in the keyword generator tool database 310. The user may then identify a format for the vendor specific files at block 407 (e.g., patient comma separated 409, patient fixed position 411, provider fixed position 413, etc.). At block 415, via the mapping configuration tab 417, the user may configure a mapping for the selected vendor. This mapping may be stored in the keyword generator tool database 310. After the configured mappings are stored, at block 418, the user may select actual healthcare input files to be processed by the tool. These files may be of various formats including but not limited to a flat file format. At block 419, via the keyword generation form 421, the healthcare input files may be processed and stored as child tables 233. The tool will also check to make sure the input files are valid at 425, with respect to it being in a format recognized by the tool. Any errors in this check 425 may be identified in a report at block 427. After the input file validation, at block 429, the tool may generate a keyword file for the input file (stored in the child tables 233) in accordance with the stored mapping configurations.

Figure 5:
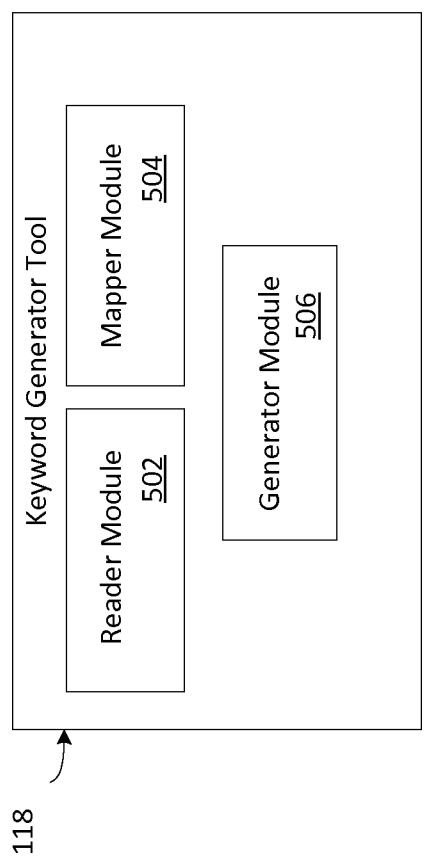
FIG. 5 is a block diagram of the keyword generator tool according to an embodiment of the disclosure.

It should be noted that the tasks described hereinthroughout may be performed by several modules including a reader module 502, a mapper module 504, and a generator module 506 as illustrated in the block diagram of FIG. 5. Generally, the reader module 502 may read any input files and store them as child tables. The mapper module 504 may allow a user to configure mappings for specific vendors. The generator module 506 may convert the stored input files, and generate keyword files in accordance with the configured mappings.

For the purposes of this specification, the term "module" includes an identifiable portion of computer code, computational or executable instructions, data, or computational object to achieve a particular function, operation, processing, or procedure. A module may be implemented in software, hardware/circuitry, or a combination of software and hardware. An identified module of executable code, for example, may comprise one or more physical or logical blocks of computer instructions that may, for instance, be organized as an object, procedure, or function. Nevertheless, the executables of an identified module need not be physically located together, but may comprise disparate instructions stored in different locations which, when joined logically together, comprise the module and achieve the stated purpose for the module. Indeed, a module of executable code could be a single instruction, or many instructions, and may even be distributed over several different code segments, among different programs, and across several memory devices. Similarly, modules representing data may be embodied in any suitable form and organized within any suitable type of data structure. The data may be collected as a single data set, or may be distributed over different locations including over different storage devices.

Figure 6:
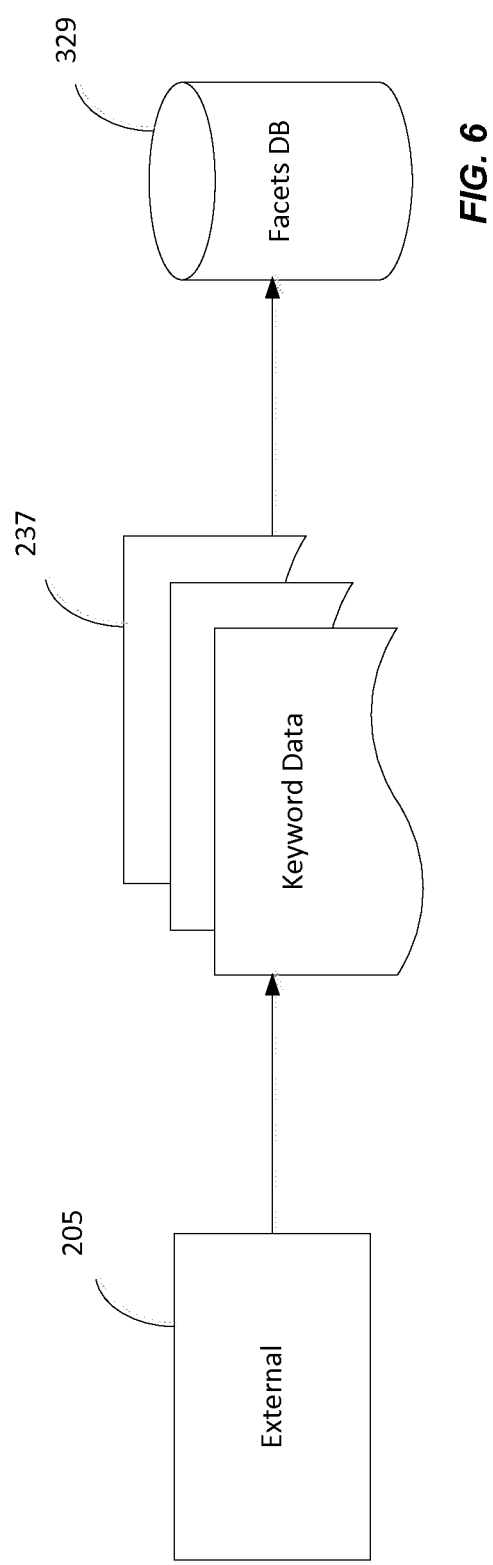
FIG. 6 is a simplified flow diagram of an illustrative embodiment of the keyword generator tool.
Figure 7A:
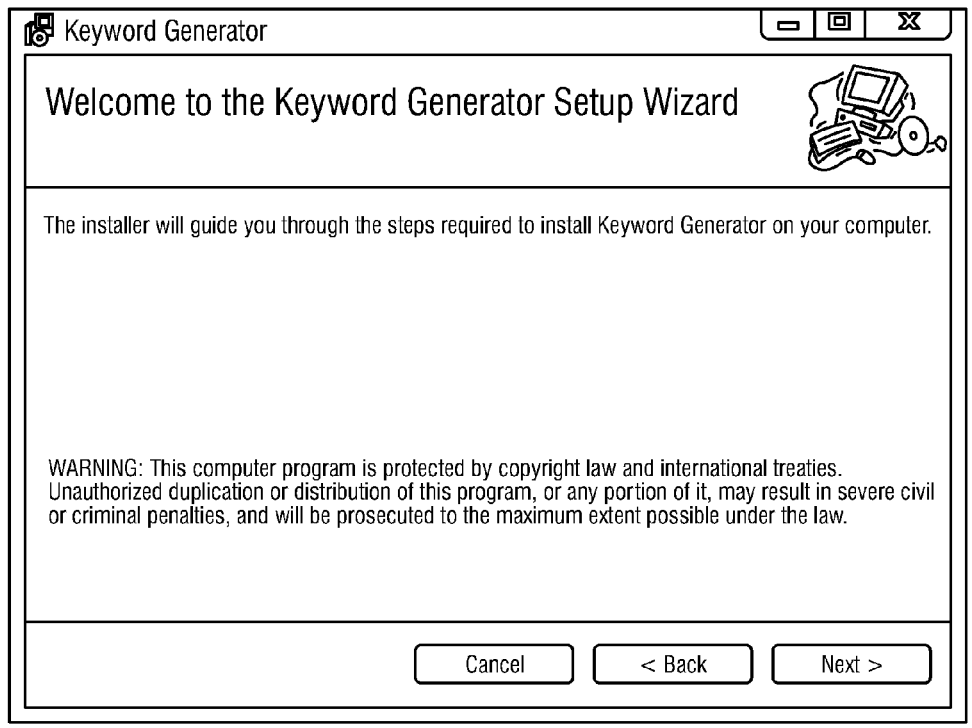
FIGS. 7-8 are example screenshots illustrating installation of the keyword generator tool of the keyword generator tool according to an embodiment of the disclosure.
Figure 7B:
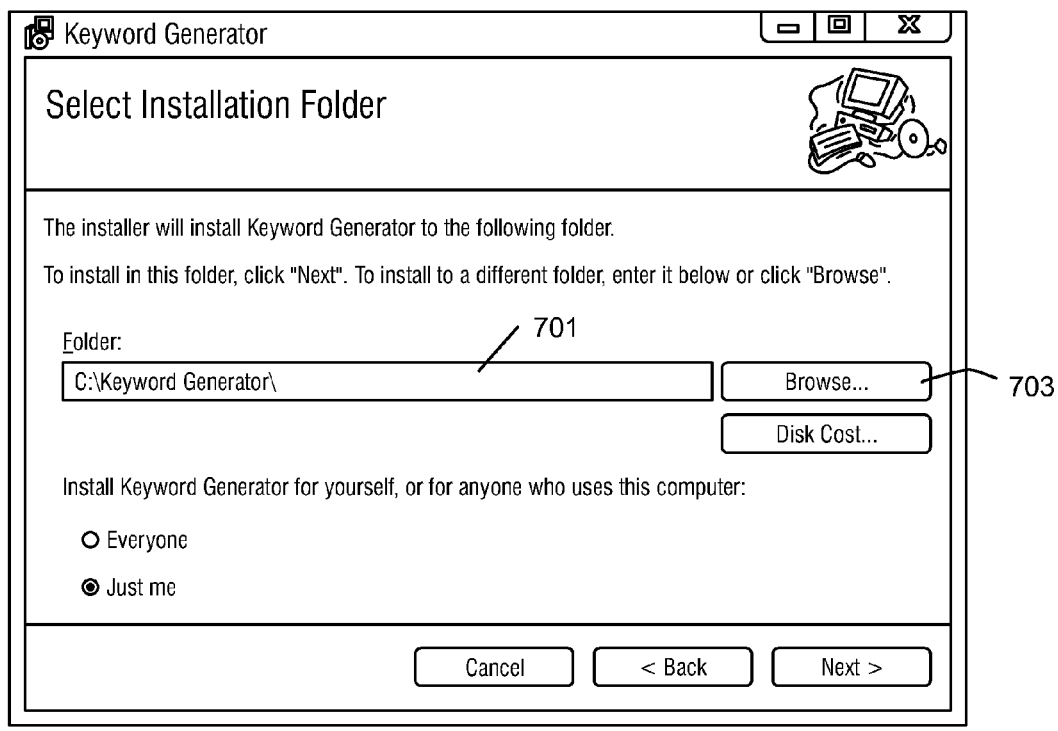
Figure 7C:
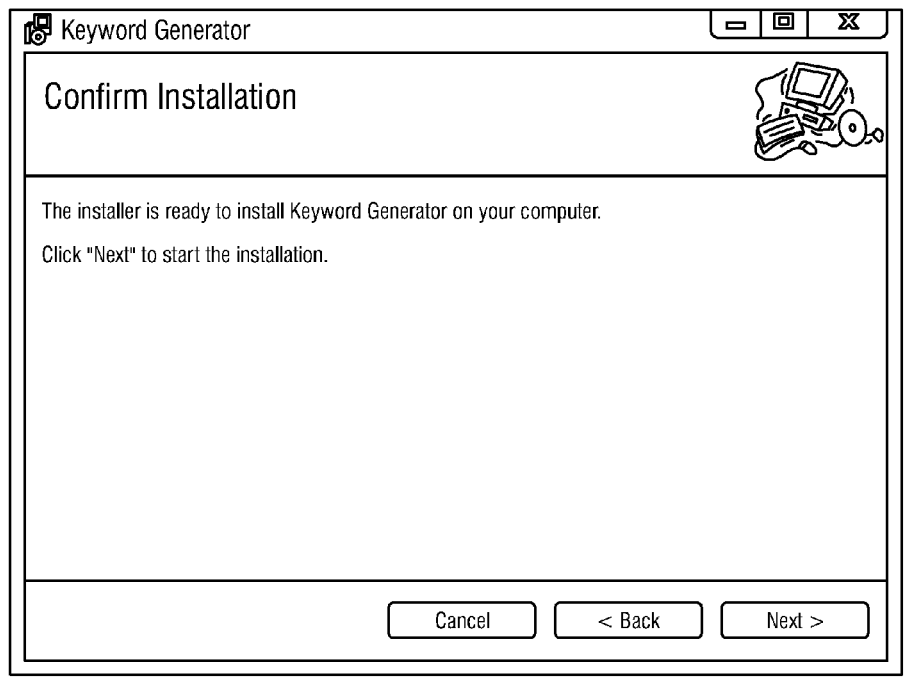
Figure 7D:
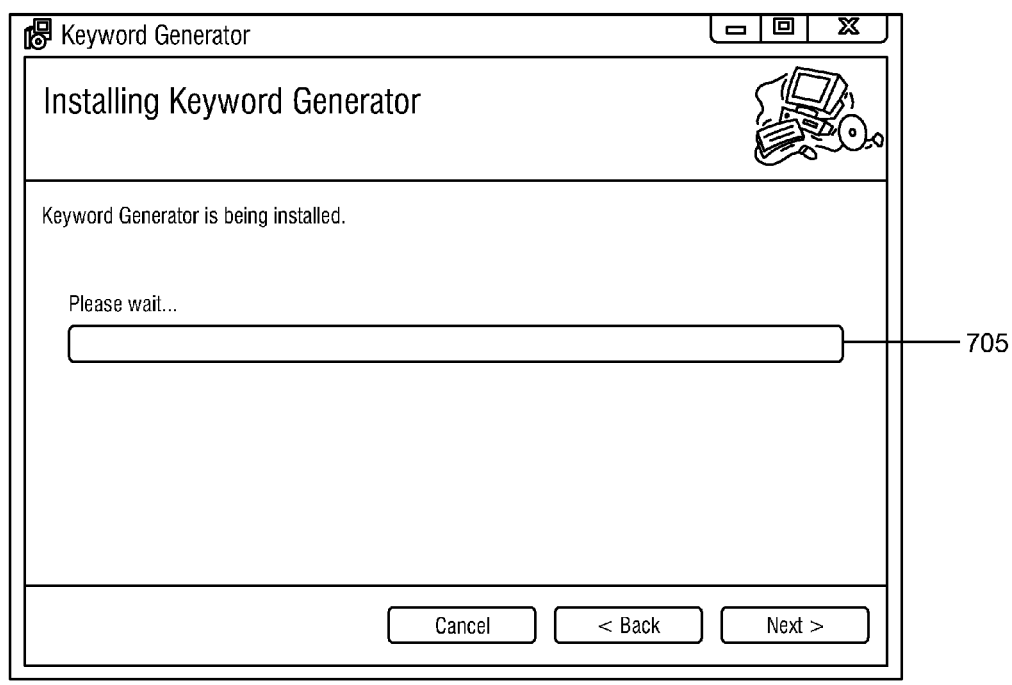

Generally speaking, and as shown in the simplified diagram of FIG. 6, embodiments of the present disclosure include a tool to integrate inbound data from external sources (e.g., input files) 205, with healthcare management system software (such as Facets™) by automating the generation of a keyword format output 237 required for loading data into healthcare management system software. The tool can be run interactively to generate keyword files for various vendor (including but not limited to healthcare patients and providers), after validation and application of business logic to the corresponding input files. These keyword files can then be stored in a database 329 of the healthcare management system.

Figure 8:
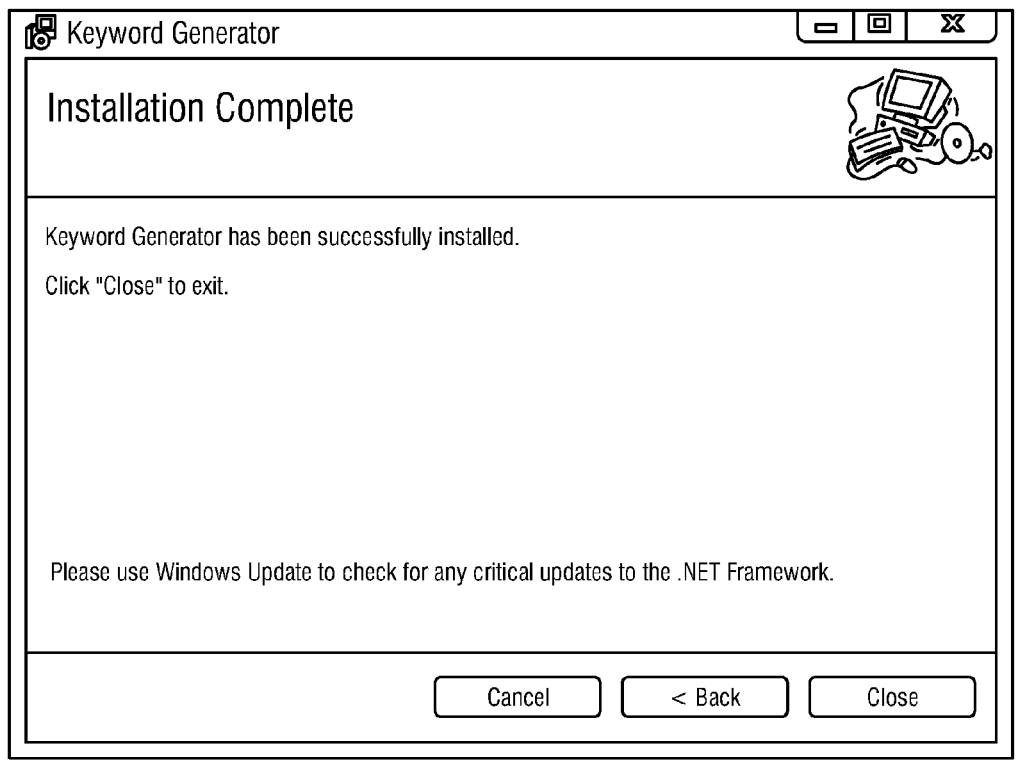

Referring now to FIGS. 7-8, example screenshots illustrating installation of the keyword generator tool are shown. FIG. 7A is an example screenshot of an installation home page. FIG. 7B is an example screenshot allowing a user to designate a location in which to install the keyword generator tool. The user is able to enter a location in folder field 701 or browse to a particular location through browse button 703. FIG. 7C is an example screenshot confirming the proceeding of the installation of the keyword generator tool. Upon installing, an example screenshot as shown in FIG. 7D will be displayed, illustrating progress of the installation process through progress bar 705. Upon completion of installation, an example screenshot, as shown in FIG. 8, will be displayed.

Figure 9:
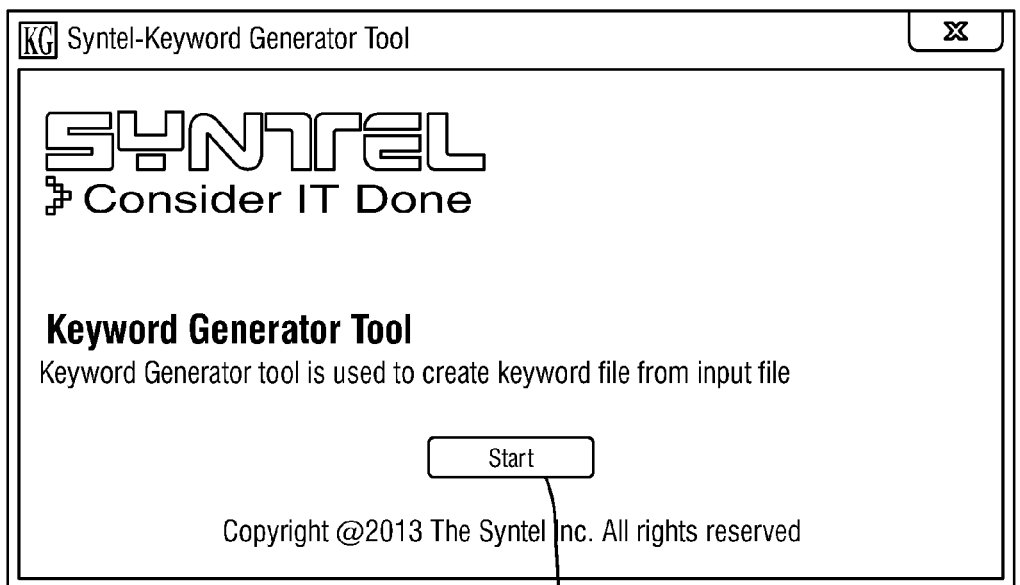
FIG. 9 is an example screenshot of a welcome screen according to an embodiment of the disclosure.
Figure 10:
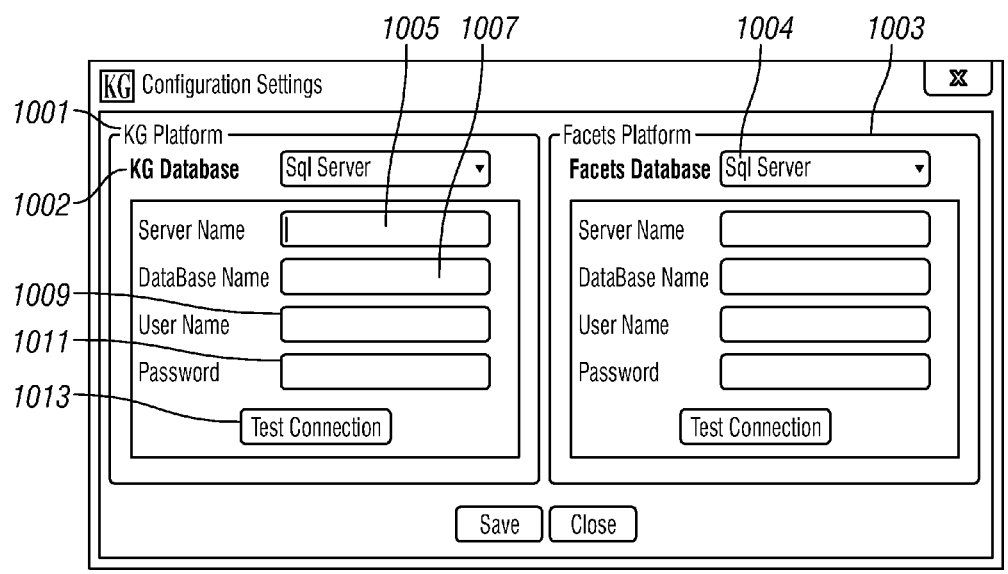
FIGS. 10-15 are example screenshots illustrating configuration settings according to an embodiment of the disclosure.
Figure 11A:
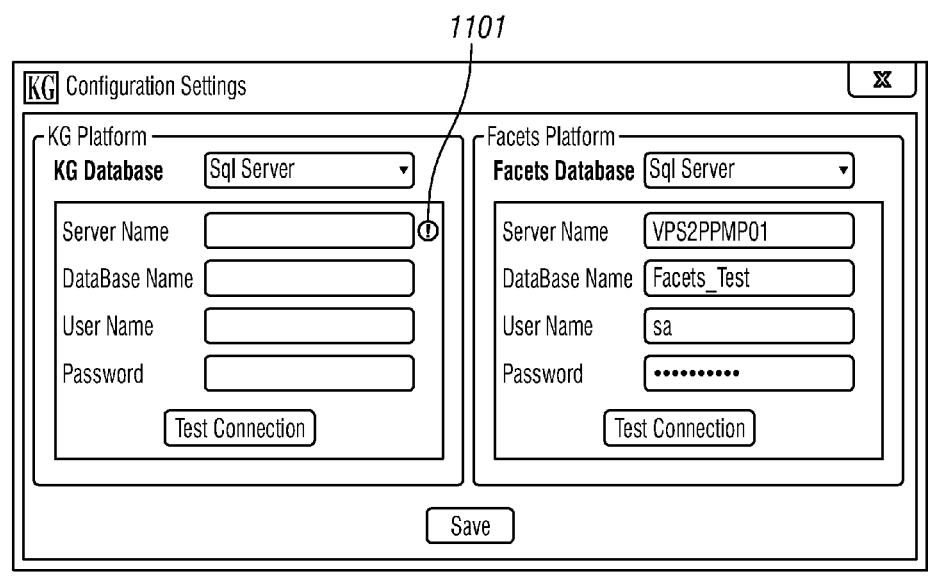
Figure 11B:
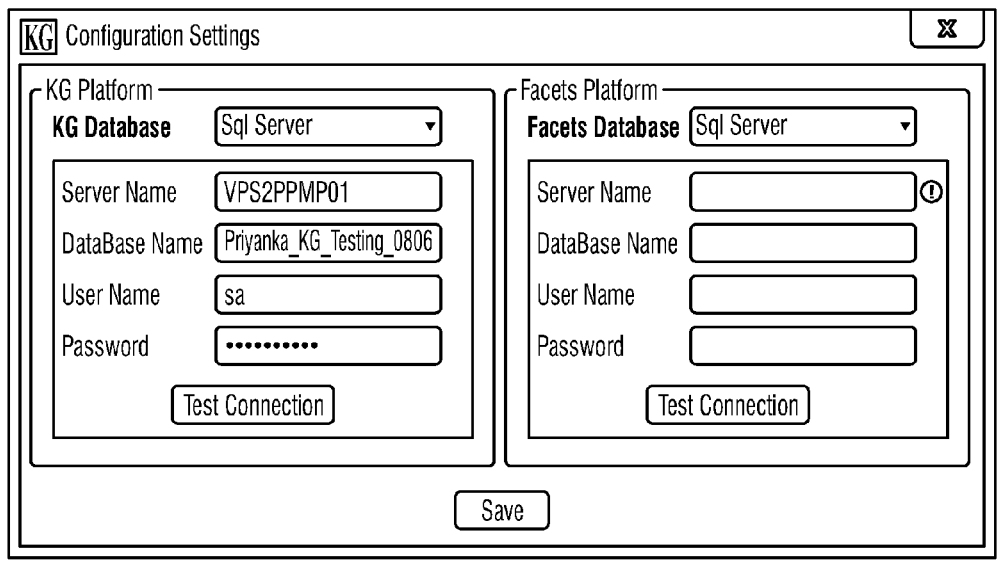
Figure 12:
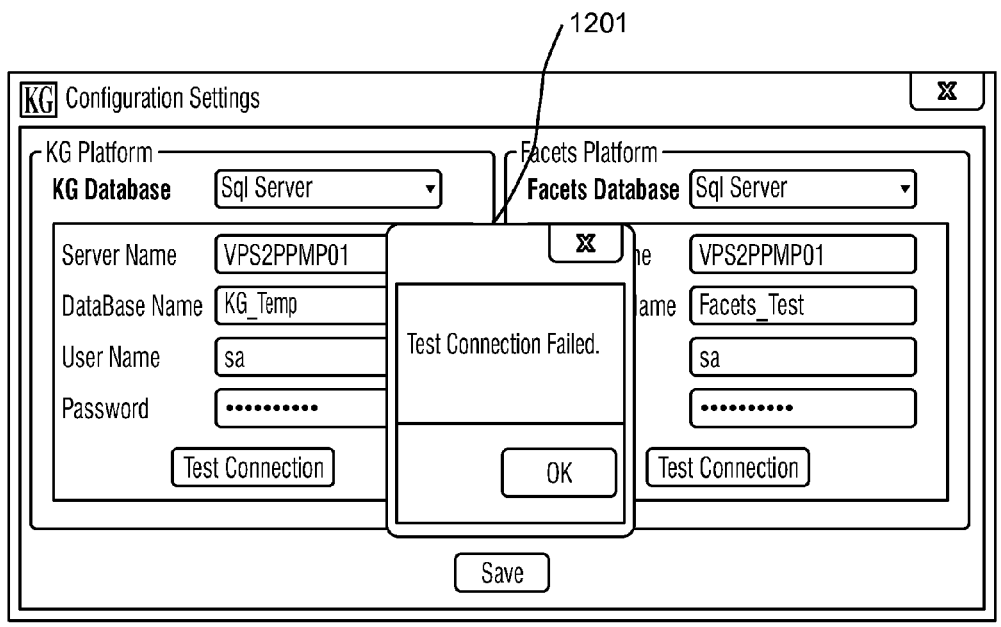
Figure 13:
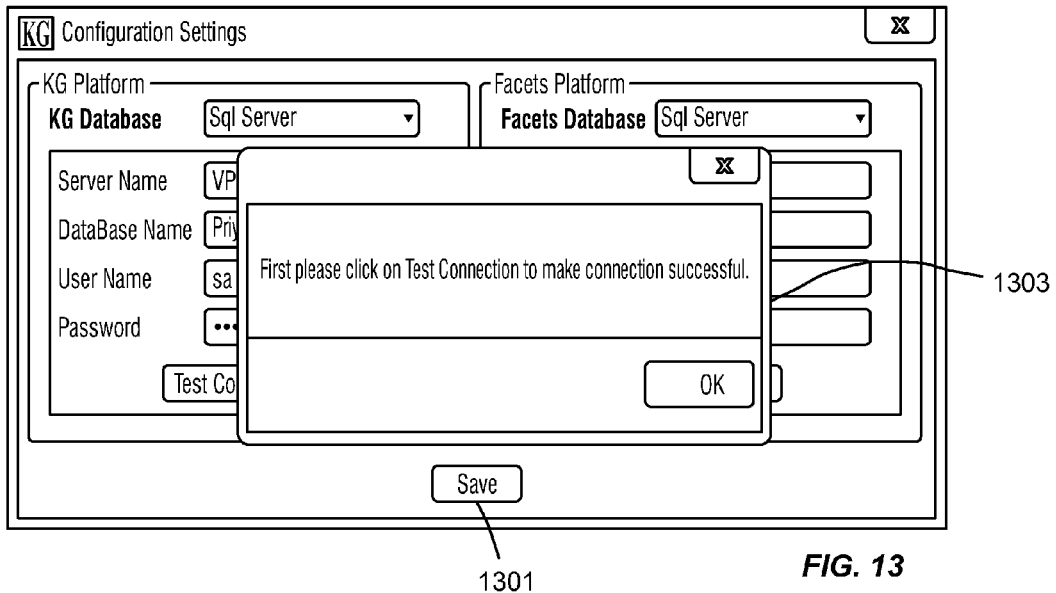
Figure 14:
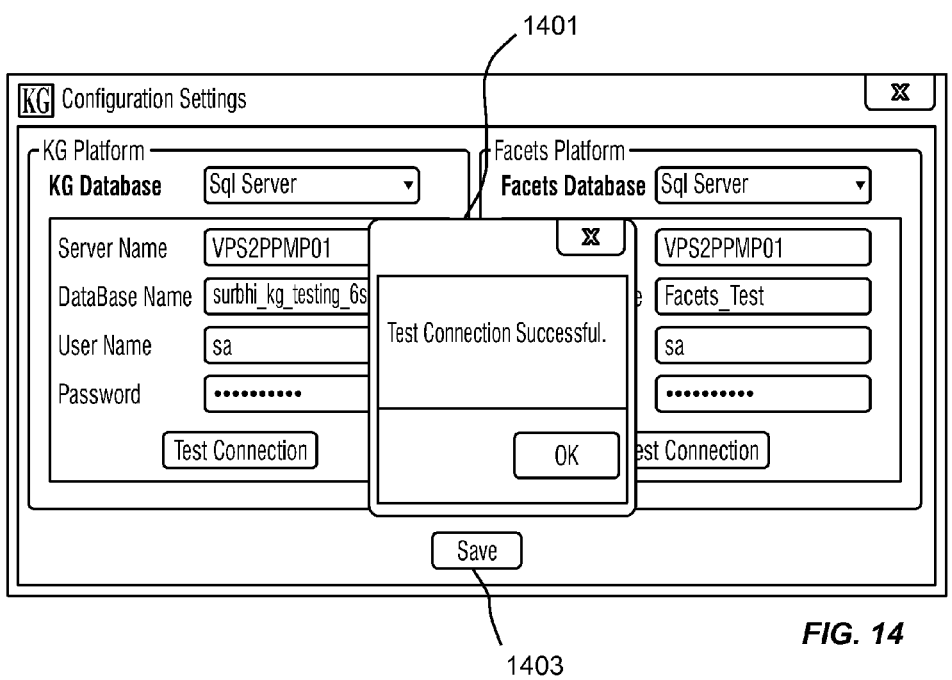
Figure 15:
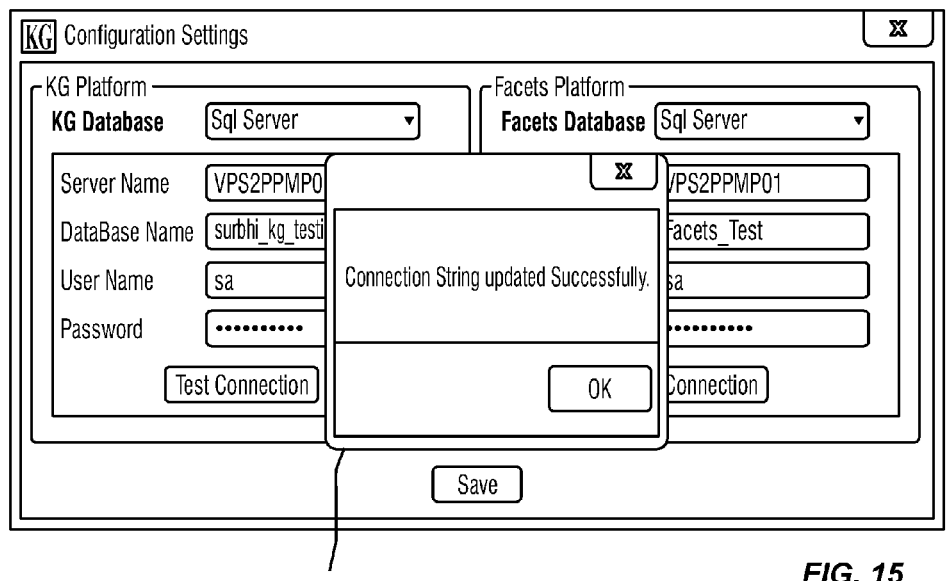

Upon loading the keyword generator tool, as shown in FIG. 9, a user is presented with a welcome screen from which the user may click start button 901 to begin using the tool. FIG. 10 is an example screenshot of a configuration settings screen for setting information about the platforms (e.g., keyword generator platform 1001 with the tool database 1002 or Facets™ platform 1003 with the Facets™ database 1004) used and other database credentials including but not limited to a server name 1005, database name 1007, user name 1009, and password 1011 for the keyword generator and Facets platform respectively. The keyword generator tool allows a user the ability to test the validity of the credentials of the respective platforms by clicking a test connection button 1013. As an example, if a user clicks on the test connection button 1013 without entering any value, an error sign 1101 may be displayed, as shown in the example screenshot in FIG. 11. Moreover, if invalid data is entered, a window 1201 may be displayed stating: "Test Connection Failed," as shown in the example screenshot in FIG. 12. Referring now to FIG. 13, if a user clicks on a save button 1301 after a tested connection has failed, the tool will present a window button 1303 prompting the user to first click on a test connection to make the connection successful. Upon proper credentials being entered, and tested successfully, the user will be presented with a window 1401 as shown in the example screenshot in FIG. 14. Next, upon clicking a save button 1403, the user is presented with a window 1501 as shown in FIG. 15, stating "Connection String updated Successfully."

Figure 16:
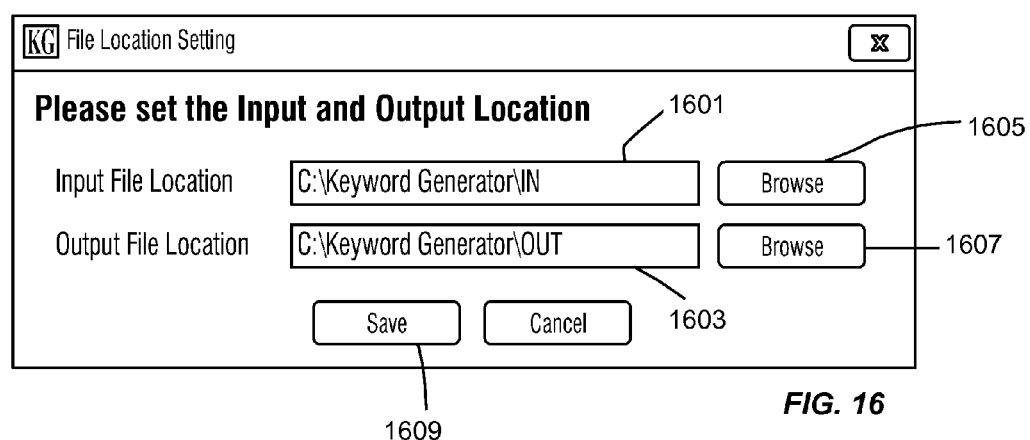
FIGS. 16-20 are example screenshots illustrating configuration options of file location settings according to an embodiment of the disclosure.
Figure 17:
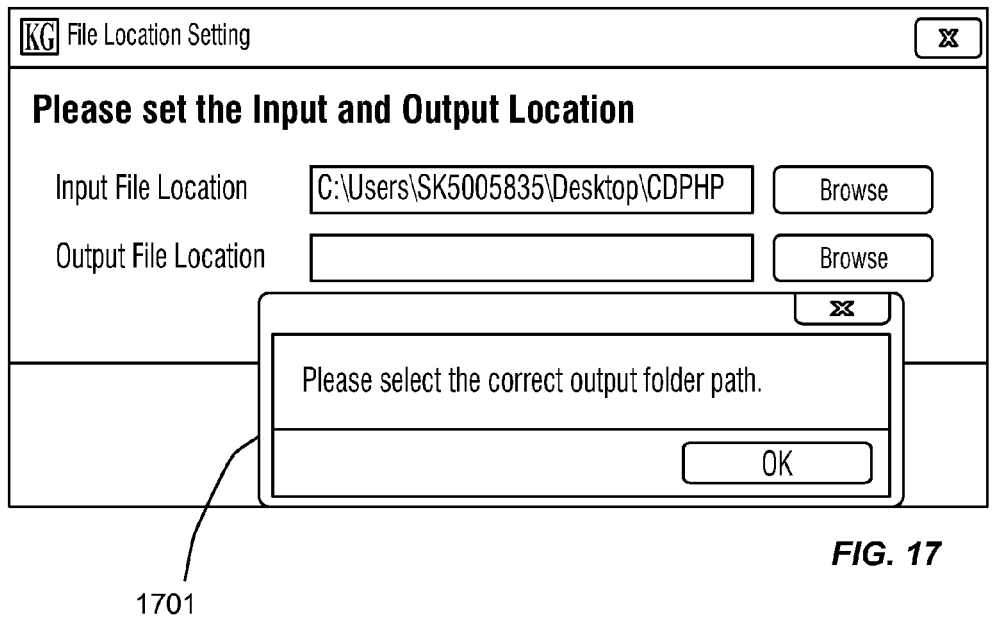
Figure 18:
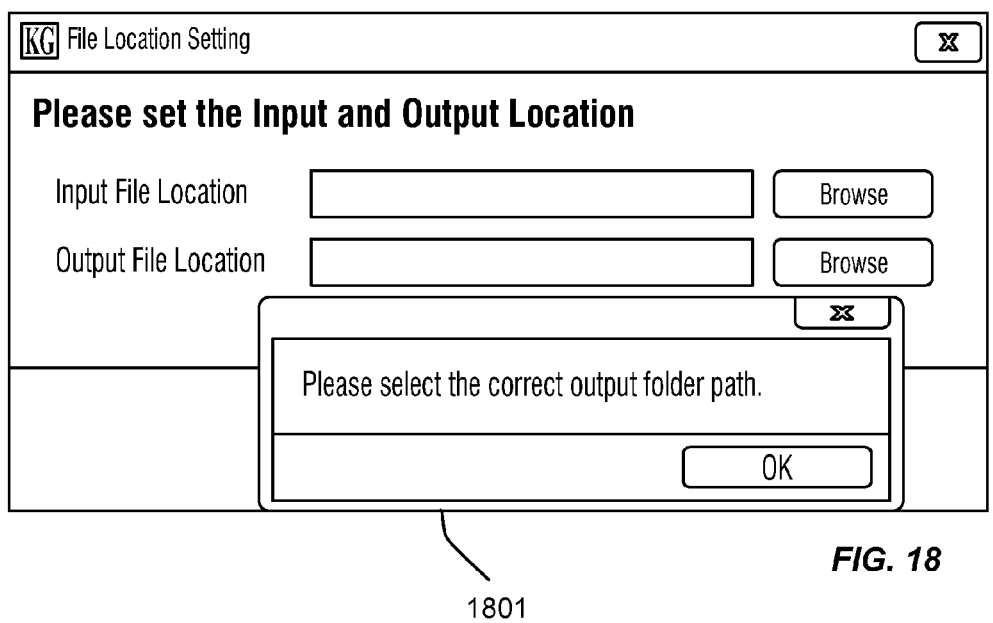
Figure 19:
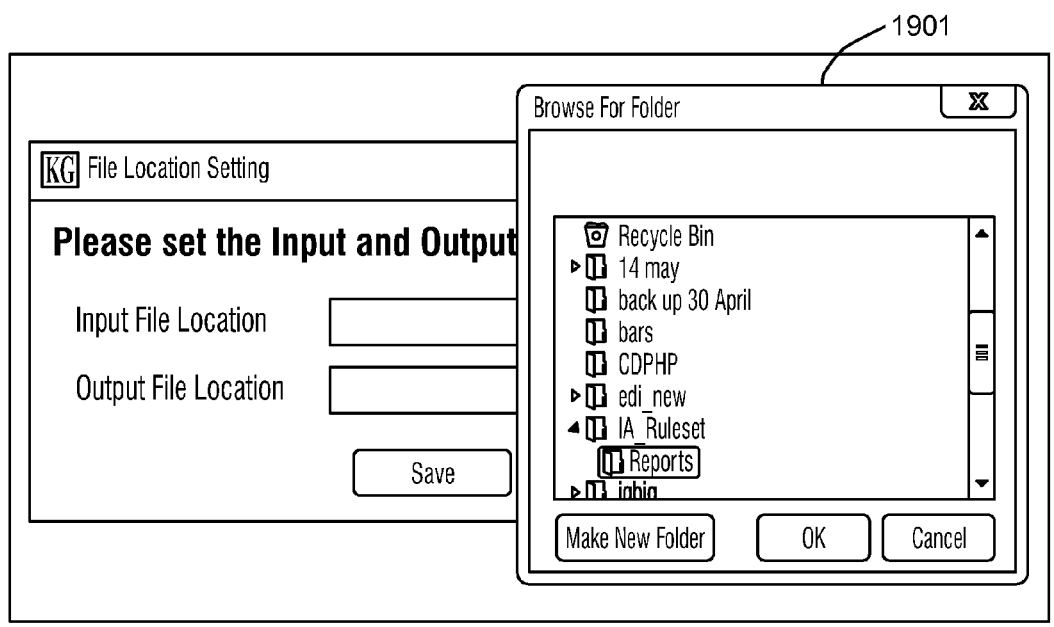
Figure 20:
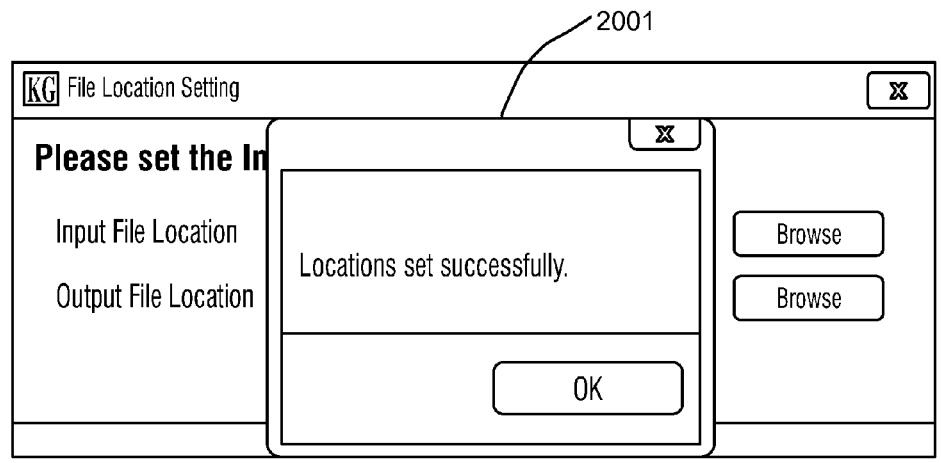

Referring now to FIGS. 16-20, example screenshots illustrating configuration options of the file location settings are shown. For example, as shown in FIG. 16, a user can set input and output file locations by entering specific locations in fields 1601 and 1603 respectively. Alternatively, the user may browse for a specific location for input and output file locations by clicking on the respective browse buttons 1605 and 1607. The tool will specify when one or both of the file locations has not been entered. For example, if only the input file location has been entered, upon attempting to save, as shown in the example screenshot in FIG. 17, a window 1701 will prompt the user to enter a correct output folder path. Moreover, if an input file location has not been entered, upon attempting to save these settings, a window 1801 will prompt the user to select a correct input folder path, as shown in the example screenshot in FIG. 18. Referring now to the example screenshot in FIG. 19, if a user chooses to browse for an input or output file location, a browse window 1901 will be presented, allowing a user to select a particular folder representing an input or output file location. After properly entering input and output file locations, upon saving these settings, as shown in the example screenshot in FIG. 20, a pop-up window 2001 may be displayed stating that the locations have been set successfully.

Figure 21:
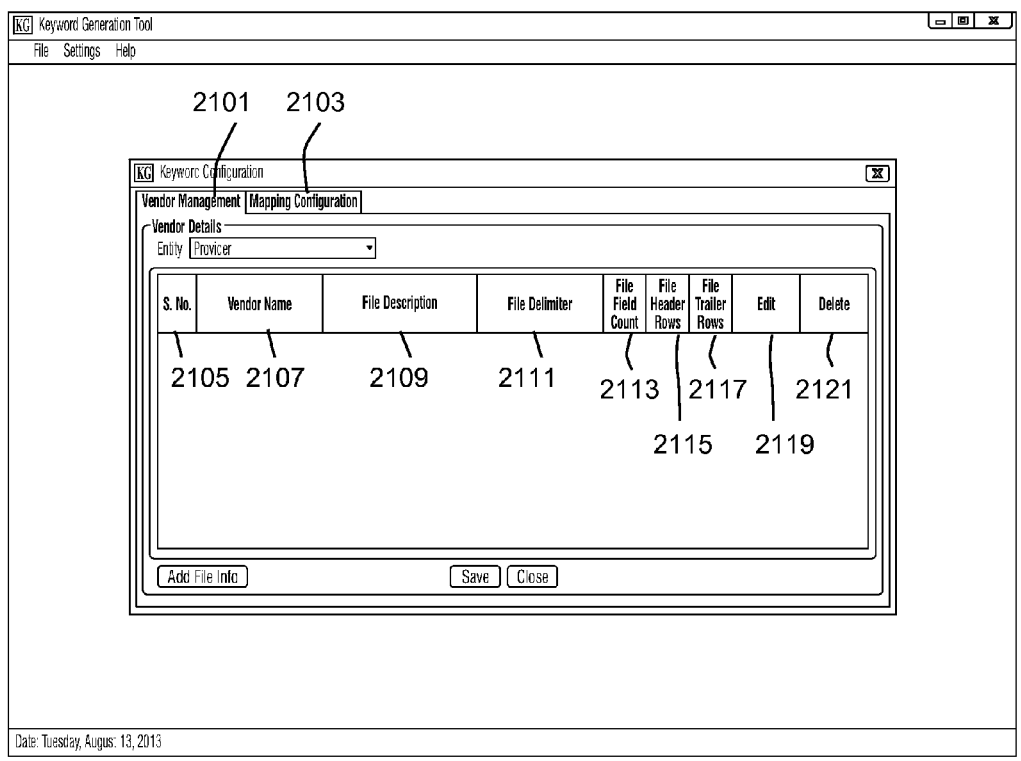
FIGS. 21-26 are example screenshots illustrating keyword configuration functionality according to an embodiment of the disclosure.

Referring now to FIG. 21, an example screenshot of a keyword configuration screen is shown. As shown, there is a vendor management tab 2101 and a mapping configuration tab 2103. By default and shown in FIG. 21, the vendor management tab 2101 is selected. With this tab 2101 selected, a user can select a type of vendor entity (e.g., provider, patient, unification management "UM", and the like) from entity drop down box 2103. By default and shown in FIG. 21, provider entity is selected. In a dominant window of the screenshot in FIG. 21, vendor detail fields are shown including but not limited to serial number 2105, vendor name 2107, file description 2109, file delimiter 2111, file field count 2113, file header rows 2115, and file trailer rows 2117. Also shown is an edit field 2119 for editing information in the respective row. Similarly, there is a delete field 2121 for deleting a respective row of vendor information.

Figure 22A:
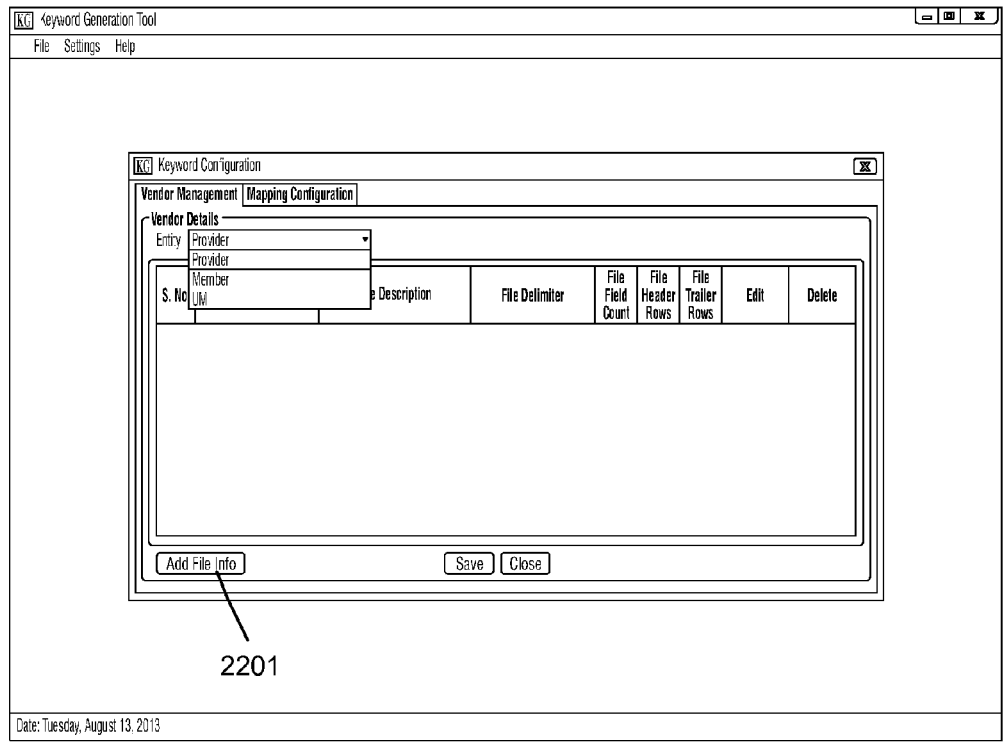
Figure 22B:
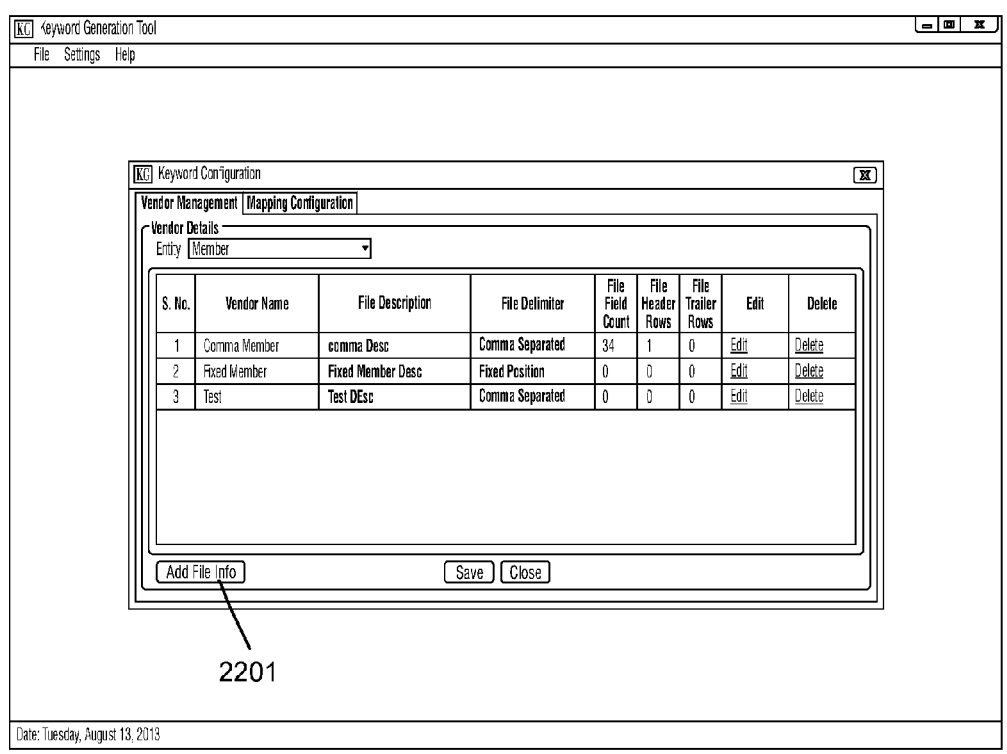

As shown in the example screenshots in FIGS. 22A and 22B, a user can add a vendor by clicking on add file info button 2201. The added vendor name will then be displayed in the grid in the dominant window. As shown, by way of non-limiting example only, three vendors are added named "comma patient", "fixed patient", and "test."

Figure 23:
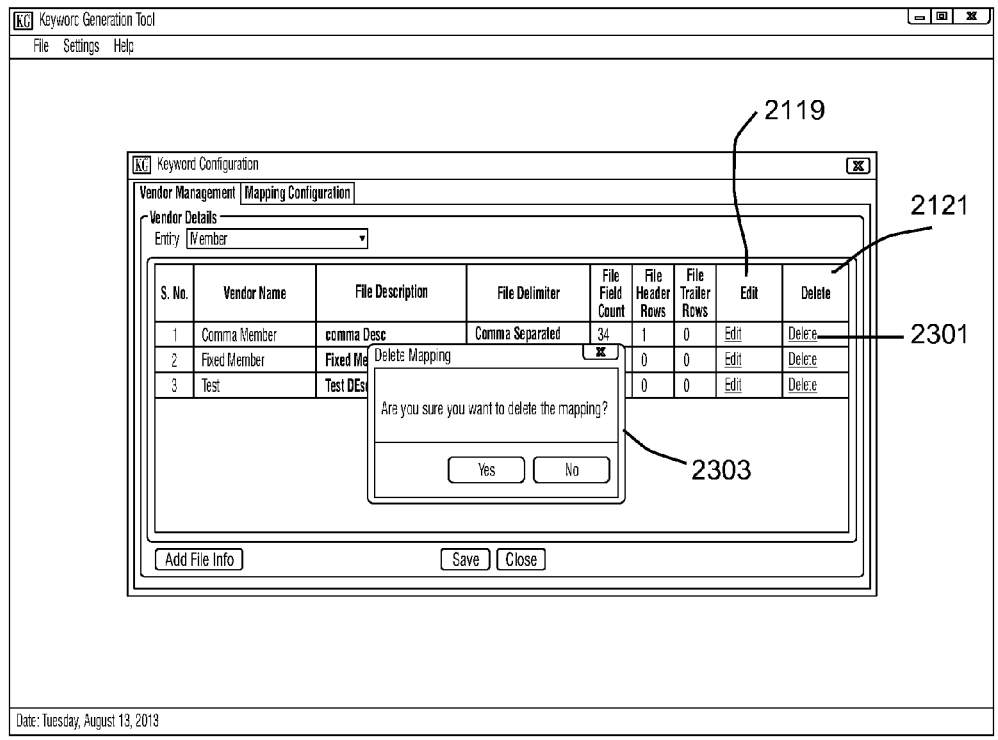
Figure 24:
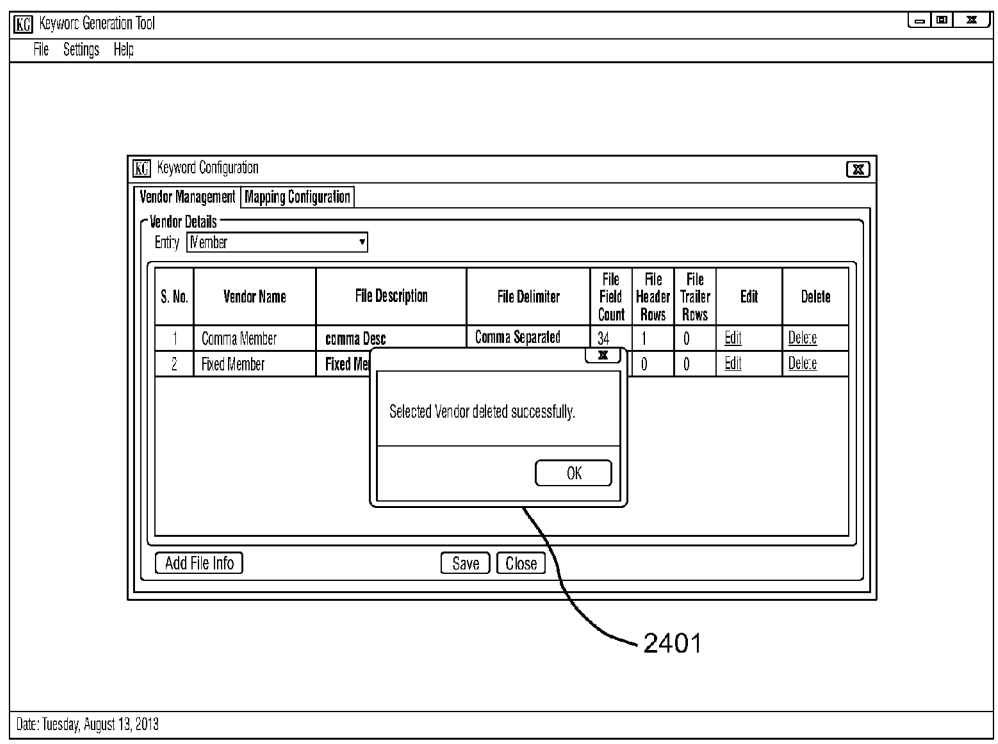

As shown in the example screenshot in FIG. 23, the tool allows for deletion of a vendor. For example, by clicking on a delete link 2301 in the delete field 2121, the vendor in the corresponding row of the delete link 2301 can be deleted. Upon clicking the delete link 2301, a pop-up window 2303 will be displayed asking a user to confirm the deletion. Upon confirmation, as shown in the example screenshot in FIG. 24, a pop-up window 2401 will be displayed stating that the selected vendor was successfully deleted.

Figure 25:
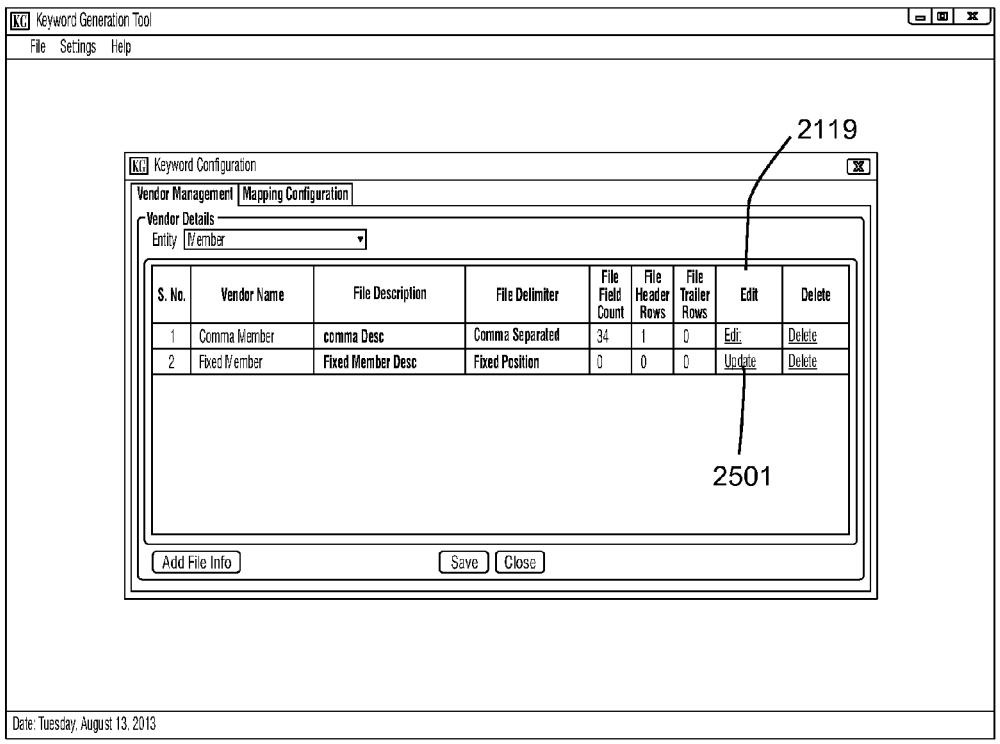
Figure 26:
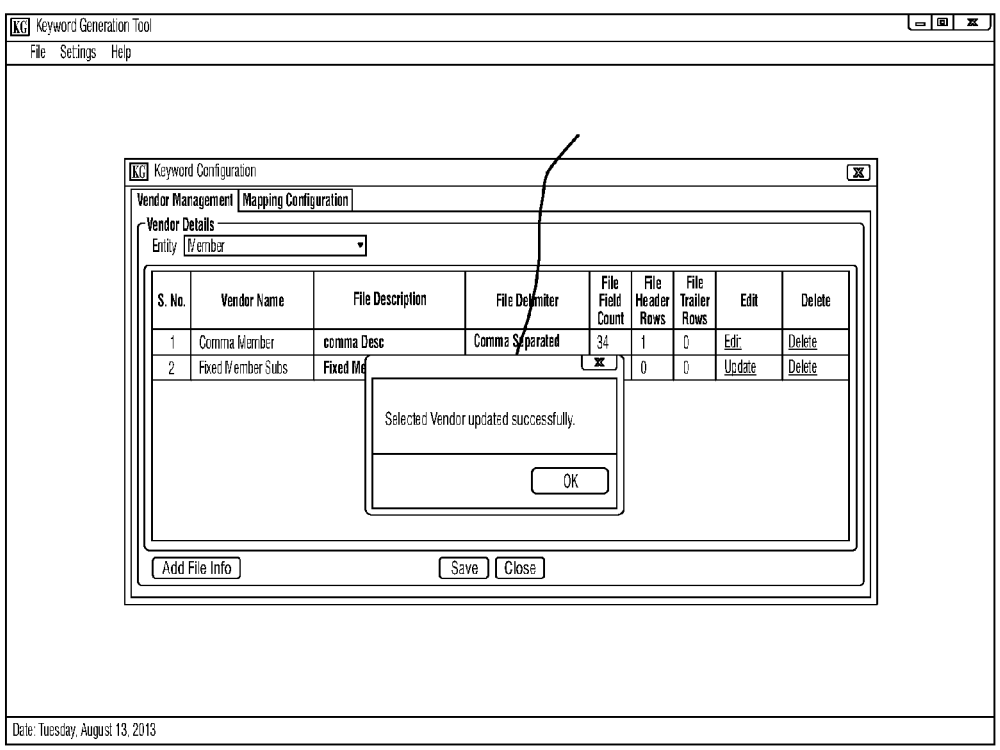

As illustrated in the example screenshot in FIG. 25, the tool allows for updating vendor information. For example, by clicking on an update link 2501 in the edit field 2119, vendor information in the corresponding row of the update link 2501 can be updated. Upon saving the update, a pop-up window 2601, as shown in the example screenshot in FIG. 26, will be displayed stating that the selected vendor information was successfully updated.

Figure 27:
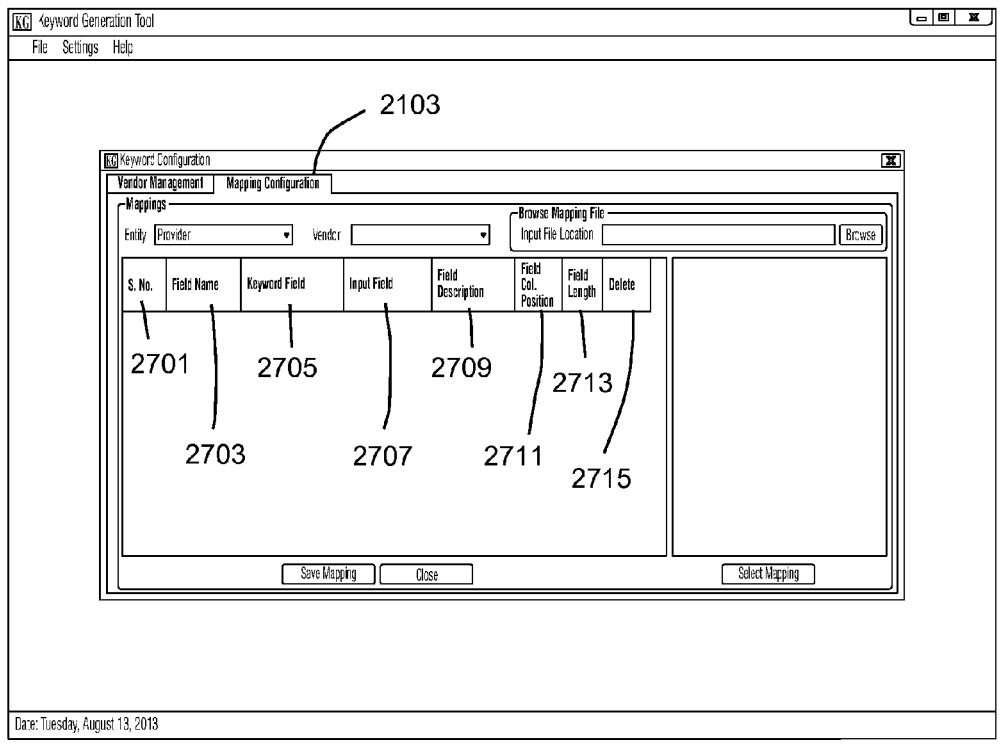
FIGS. 27-38 are example screenshots illustrating mapping configuration functionality according to an embodiment of the disclosure.
Figure 28:
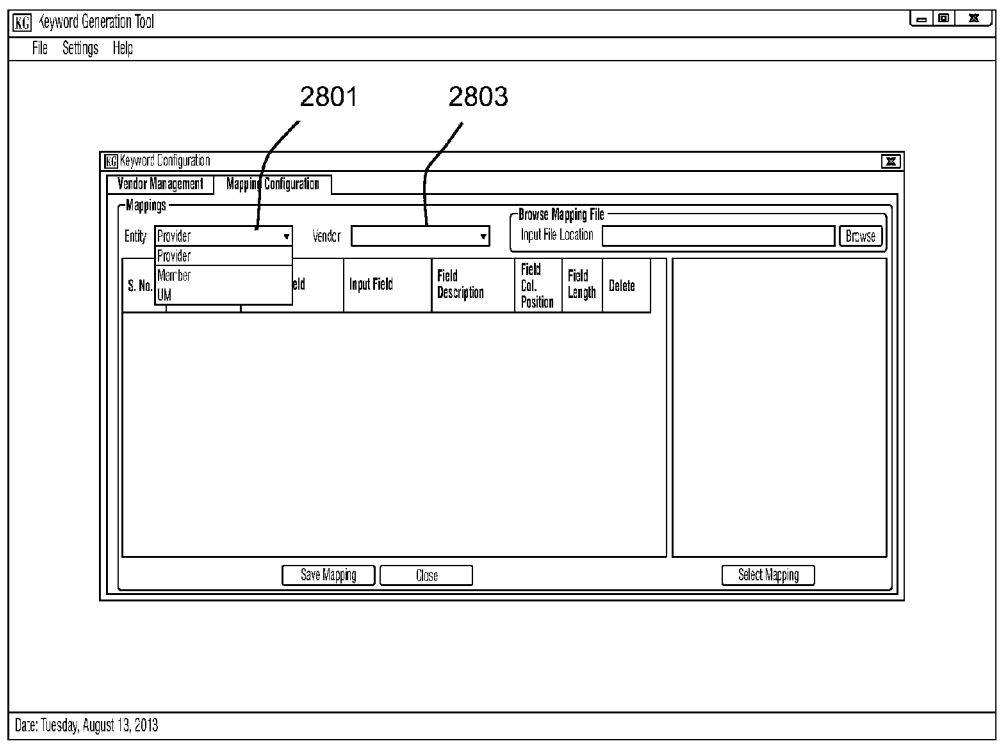

As shown in FIG. 27, by clicking on the mapping configuration tab 2103, the tool allows for configuration of mappings. In a dominant window of the screenshot in FIG. 27, mapping detail fields are shown including but not limited to serial number 2701, field name 2703, keyword field 2705, input field 2707, field description 2709, field column position 2711, field length 2713, and delete field 2715. As shown in FIG. 28, through an entity drop-down menu 2801, the user is able to select a type of entity for the vendor for the user wishing to create a mapping.

Figure 29:
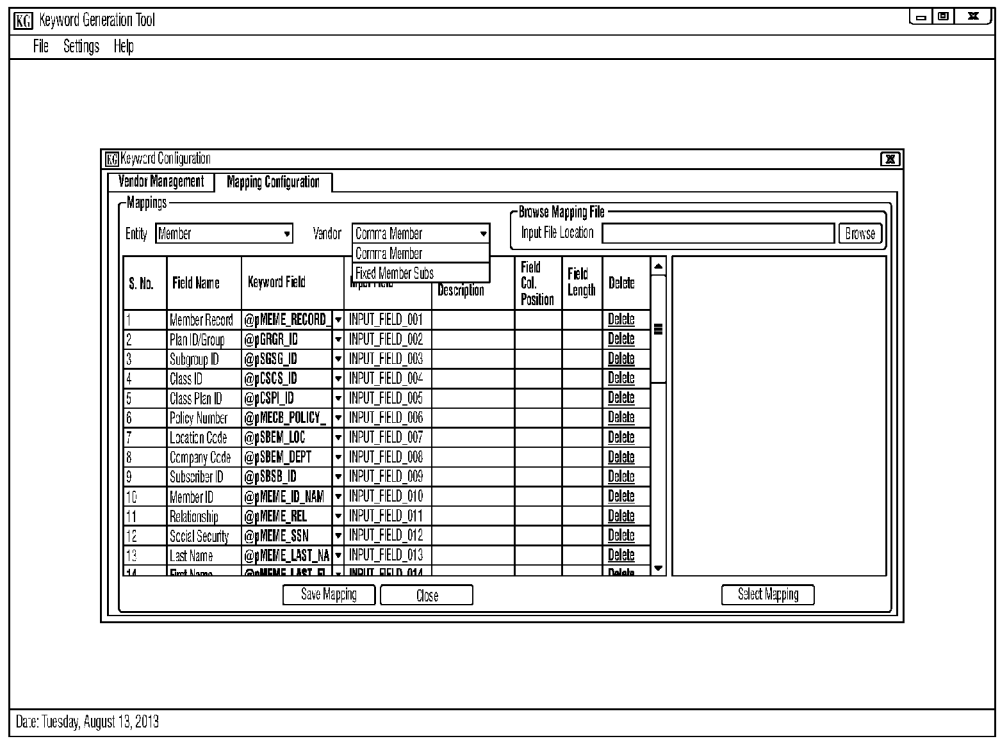
Figure 30:
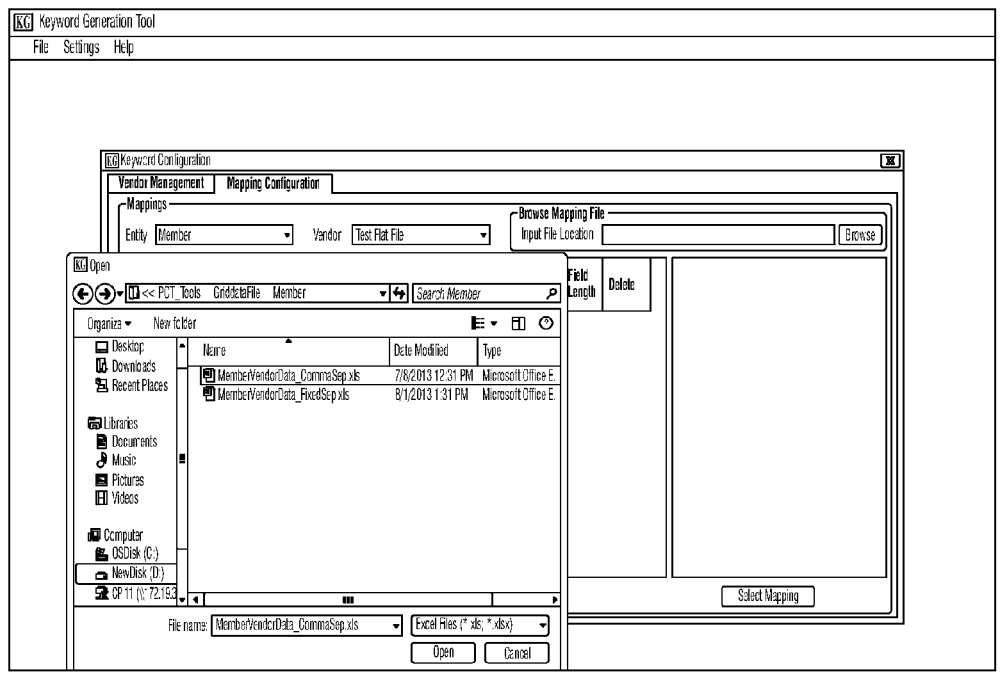

If a mapping has already been created for the selected vendor, the mapping will be displayed in a grid as shown in the example screenshot in FIG. 29. However, if mapping data is not present for the selected vendor, the user is prompted to enter (or browse) to the location of the vendor mapping data, as shown in FIG. 30.

Figure 31:
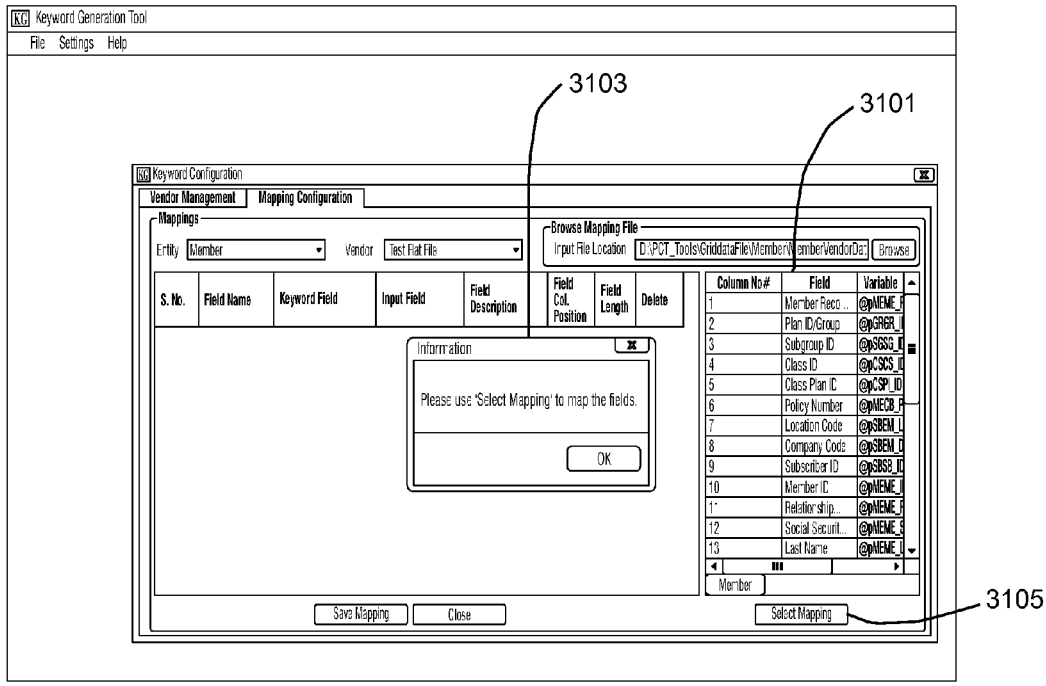
Figure 32:
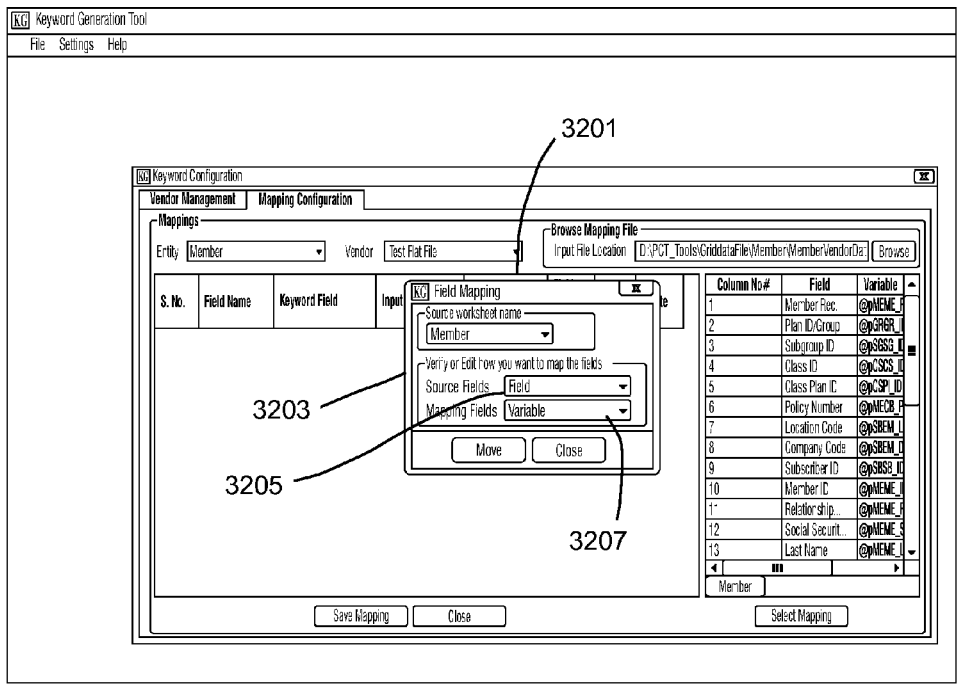
Figure 33:
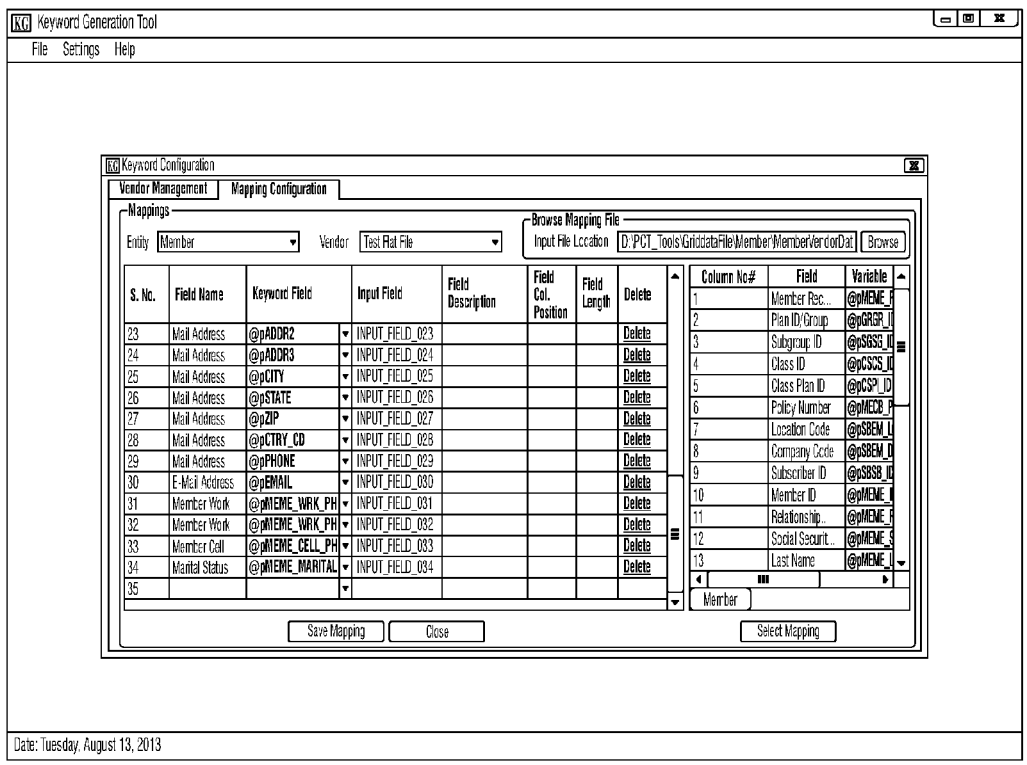

After selecting the input file, the data will get displayed in a worksheet as shown in a grid 3101 in the example screenshot in FIG. 31. A pop-up window 3103 is displayed prompting the user to select a mapping to map fields. Upon clicking a select mapping button 3105, a pop-up window 3201 is displayed prompting the user to specify details of the mapping to be performed, an example screenshot of which is shown in FIG. 32. Within the pop-up window 3201, the user can select a source worksheet name 3203 to be mapped, specific fields 3205 to be mapped, and specific mapping fields 3207 to which these specific fields are to be mapped. Referring now to the example screenshot in FIG. 33, the selected rows of fields and their respective mappings are displayed. For example, as shown in FIG. 33, for the vendor name "test flat file", the row specified as serial no. 30 has a field name of "email address" which is configured to be mapped to keyword field "@pEMAIL."

Figure 34A:
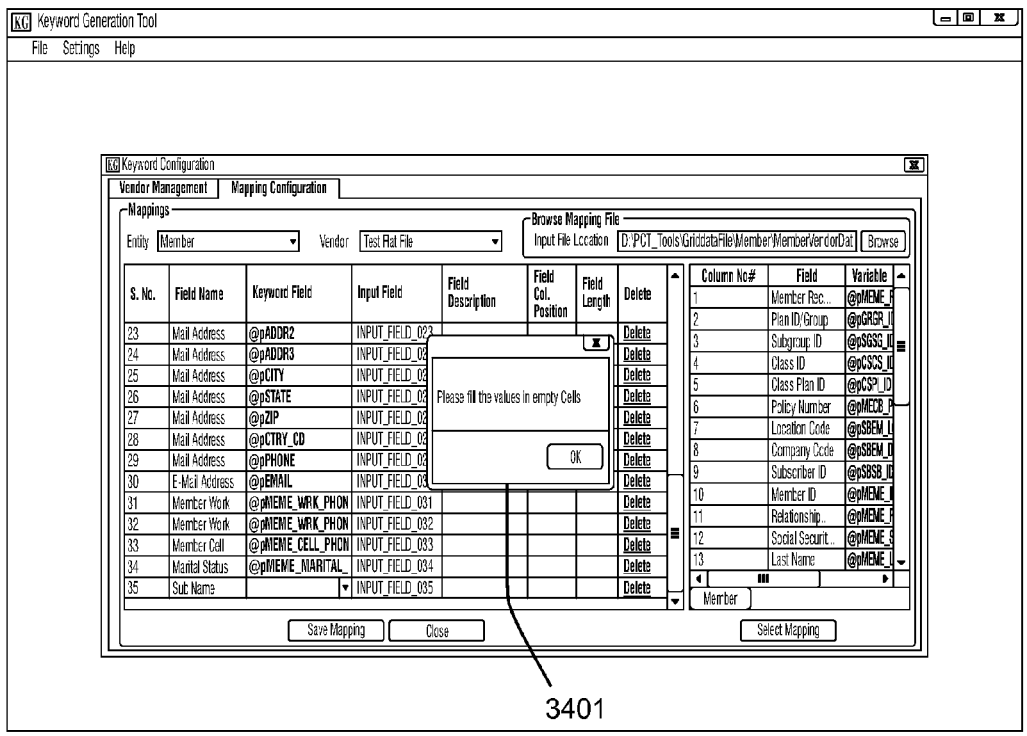
Figure 34B:
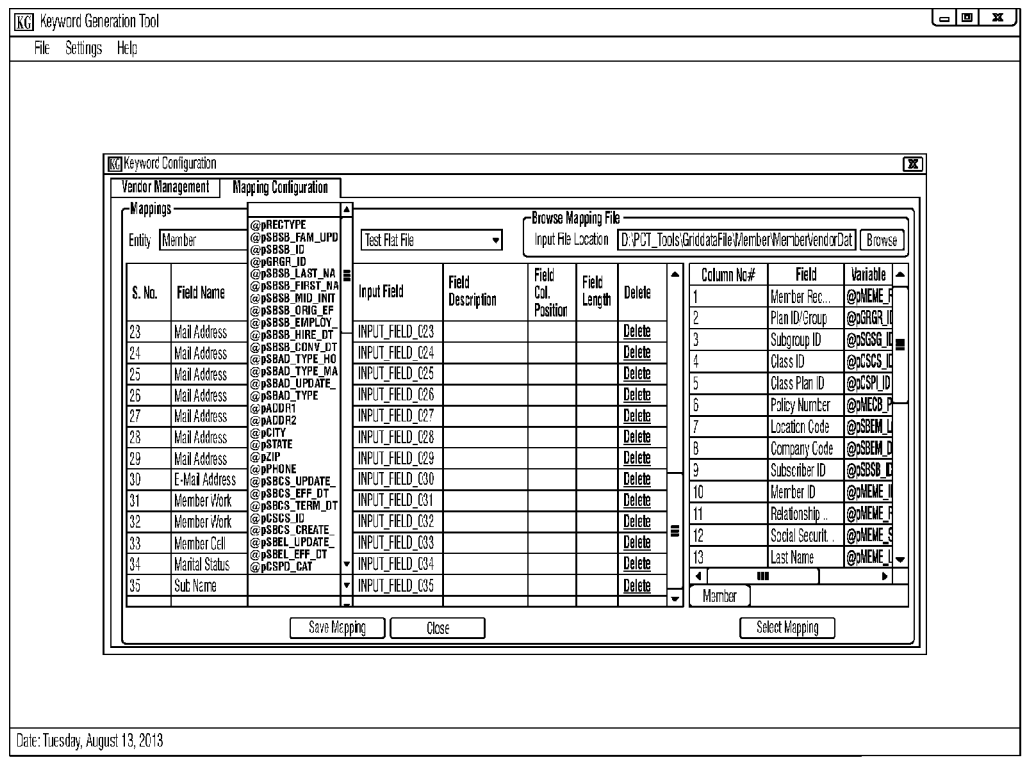

If a keyword field is empty, the user may be prompted to enter a value in the empty keyword field, via pop-up window 3401 as shown in example screenshot in FIG. 34A. Proper values can be entered as shown in FIG. 34B.

Figure 35:
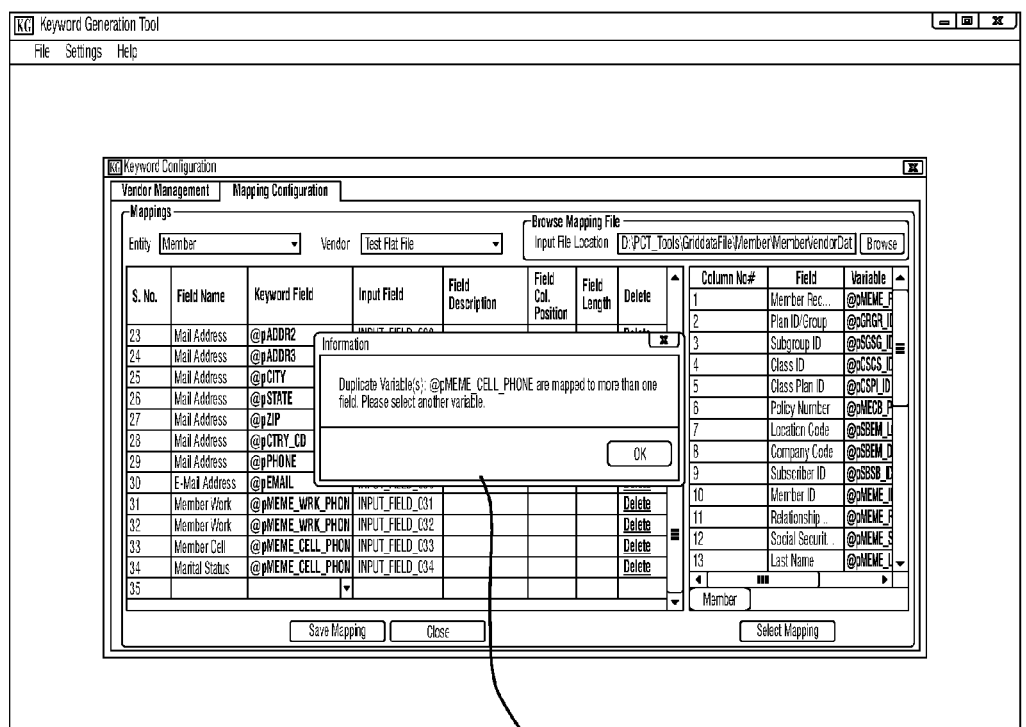

The tool also is able to detect when more than one field of a vendor file is to be mapped to the same keyword field. When this occurs, an example screenshot as shown in FIG. 35 is displayed. As shown, a pop-up window 3501 is displayed identifying the duplicate fields.

Figure 36:
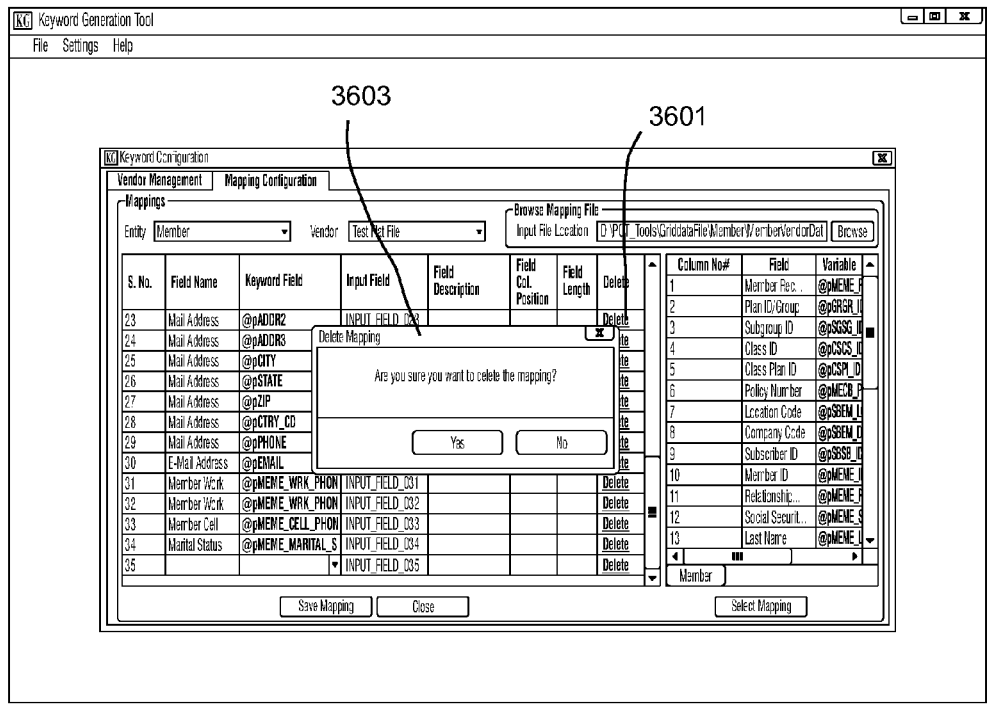
Figure 37:
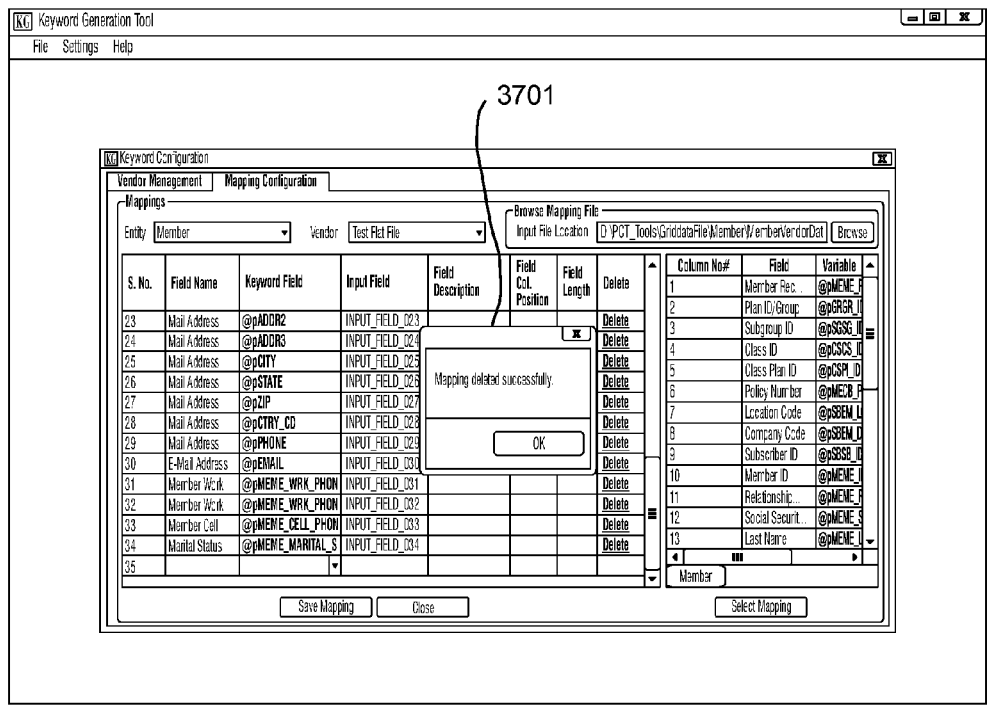
Figure 38:
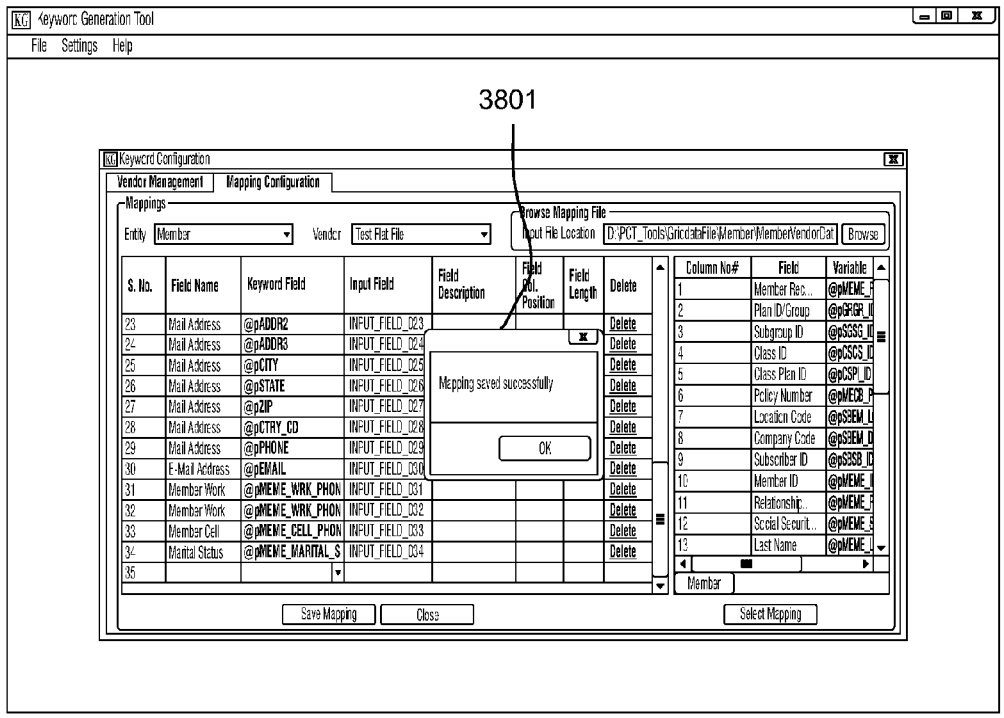

FIG. 36 is an example screenshot illustrating how a user can delete a particular keyword field value. By clicking on a delete link 3601, the keyword field value in the corresponding row may be deleted. A pop-up window 3603 is displayed asking the user to confirm the selected deletion. Upon confirmation, a pop-up window 3701 is displayed stating that the deletion was successful. An example screenshot of this pop-up window 3701 is shown in FIG. 37. Upon saving a mapping, a user is presented with a screen as shown in FIG. 38. A pop-up window 3801 may be displayed stating that the mapping was saved successfully.

Figure 39A:
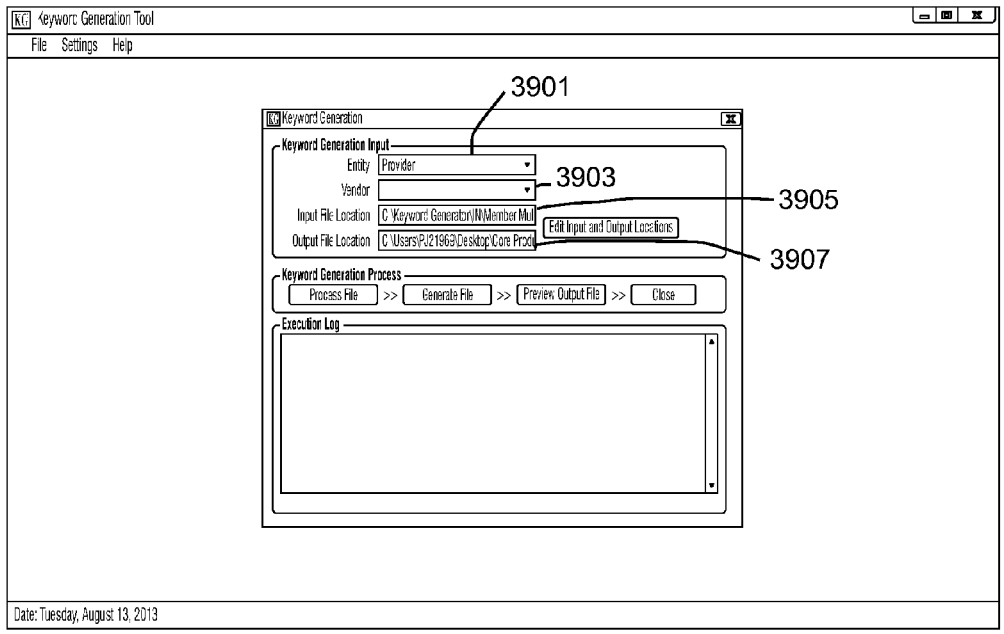
FIGS. 39A-45 are example screenshots illustrating keyword generation functionality according to an embodiment of the disclosure.
Figure 39B:
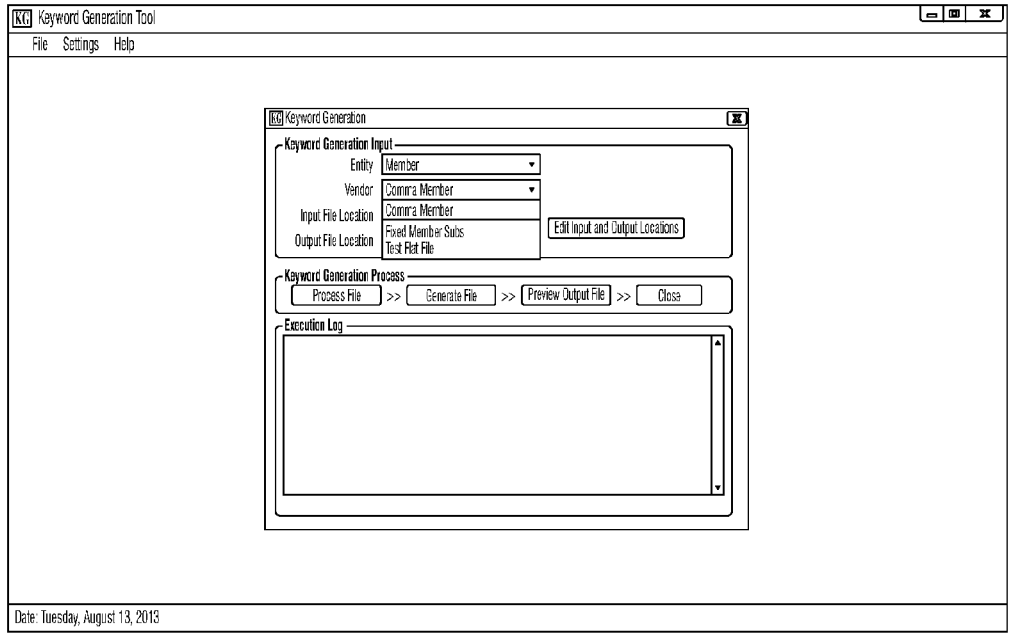
Figure 40A:
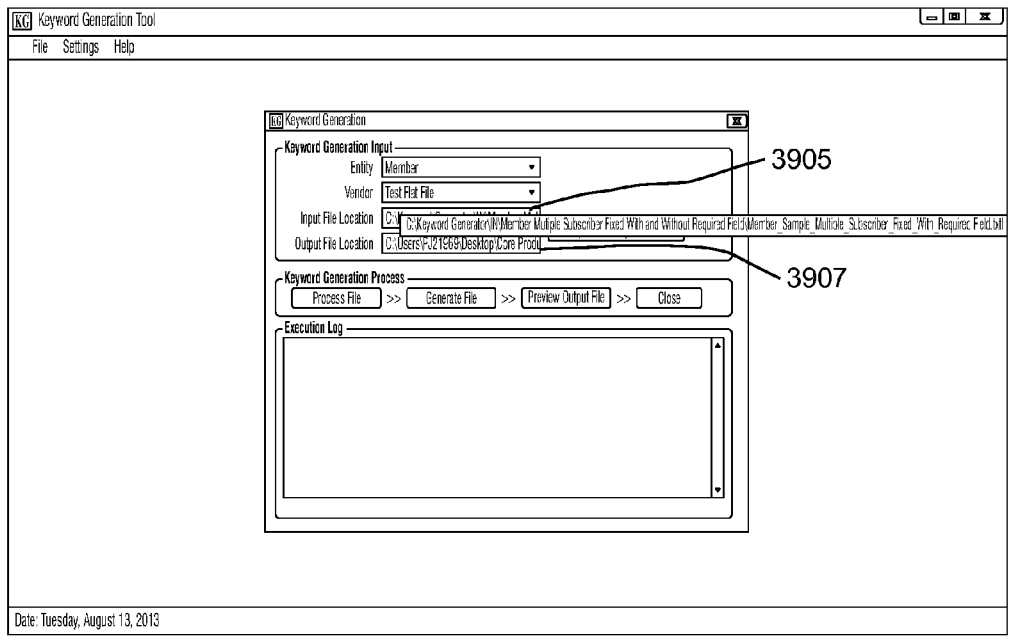
Figure 40B:
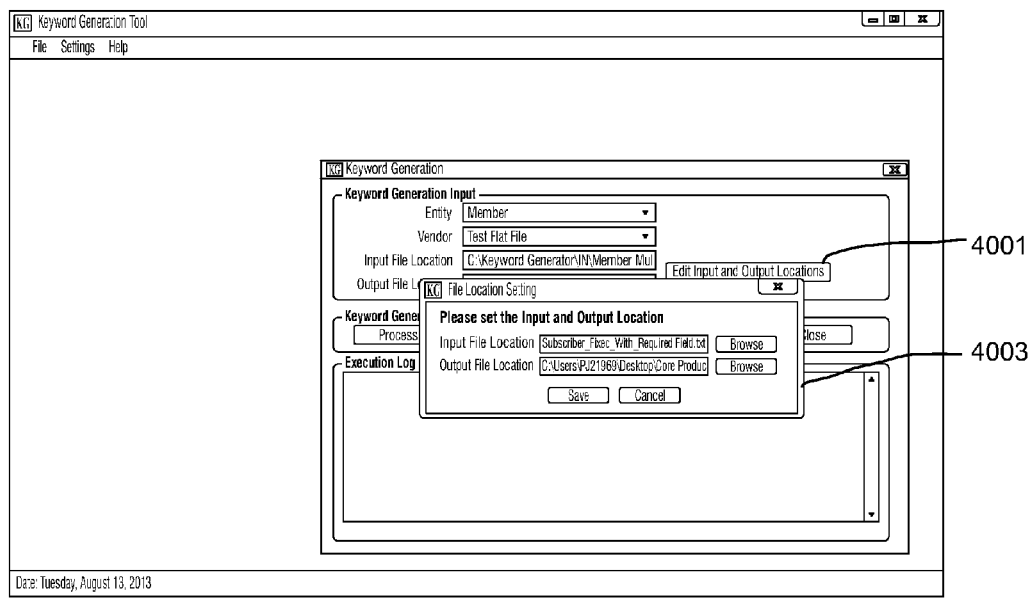

FIGS. 39A and 39B are example screenshots of a keyword generation main menu screen. From this screen, a user is able to select a type of entity 3901, vendor 3903, input file location 3905, and output file location 3907. Referring now to FIGS. 40A and 40B, if the input file and output file locations have already been set, the locations will already be reflected in these input file and output file location fields 3905 and 3907, respectively. Alternatively, if the file locations were not previously set, a user can click on an "edit input and output locations" button 4001. A pop-up window 4003 will then be displayed from which a user can browse to where the input file can be located, as well as where the keyword output file can be stored.

Figure 41:
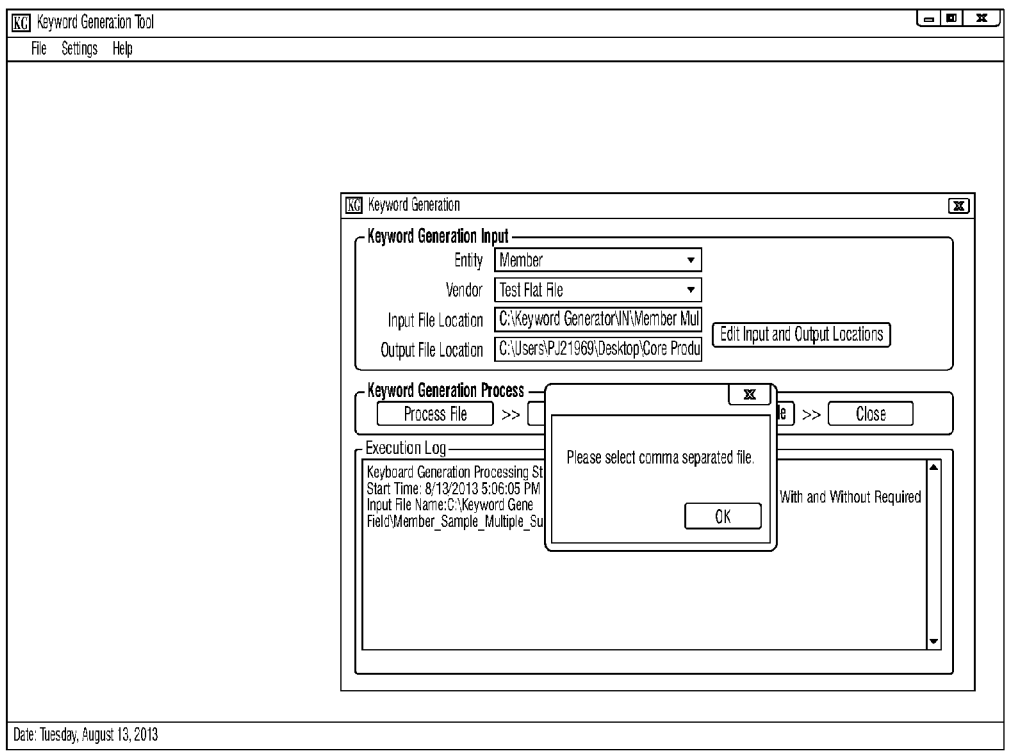
Figure 42:
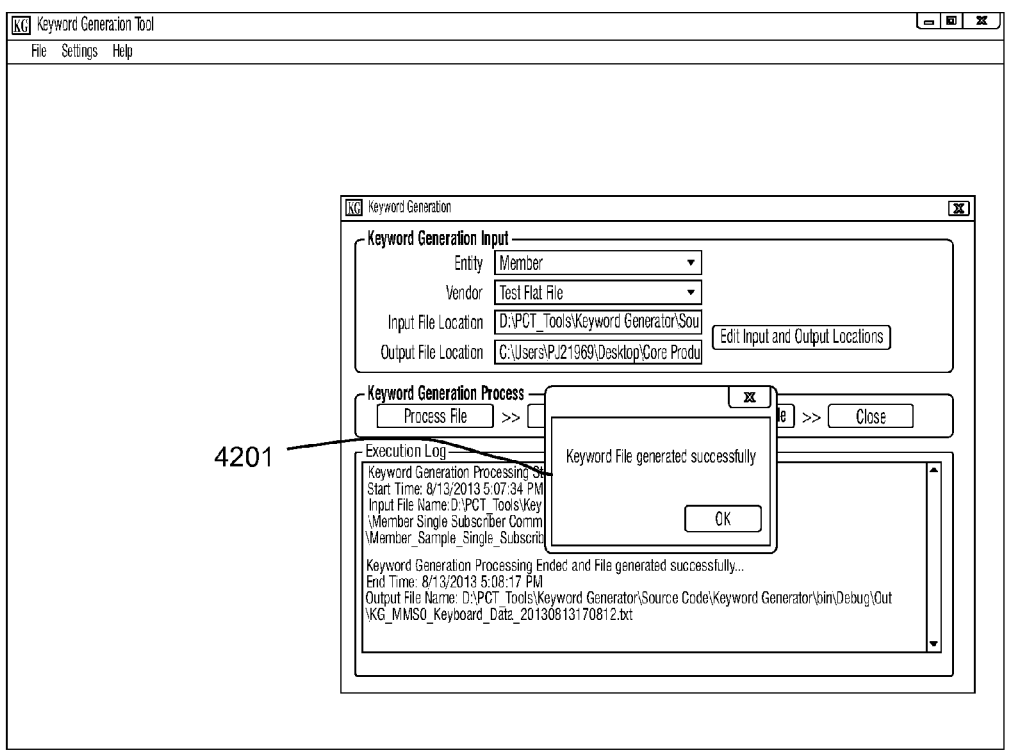
Figure 43:
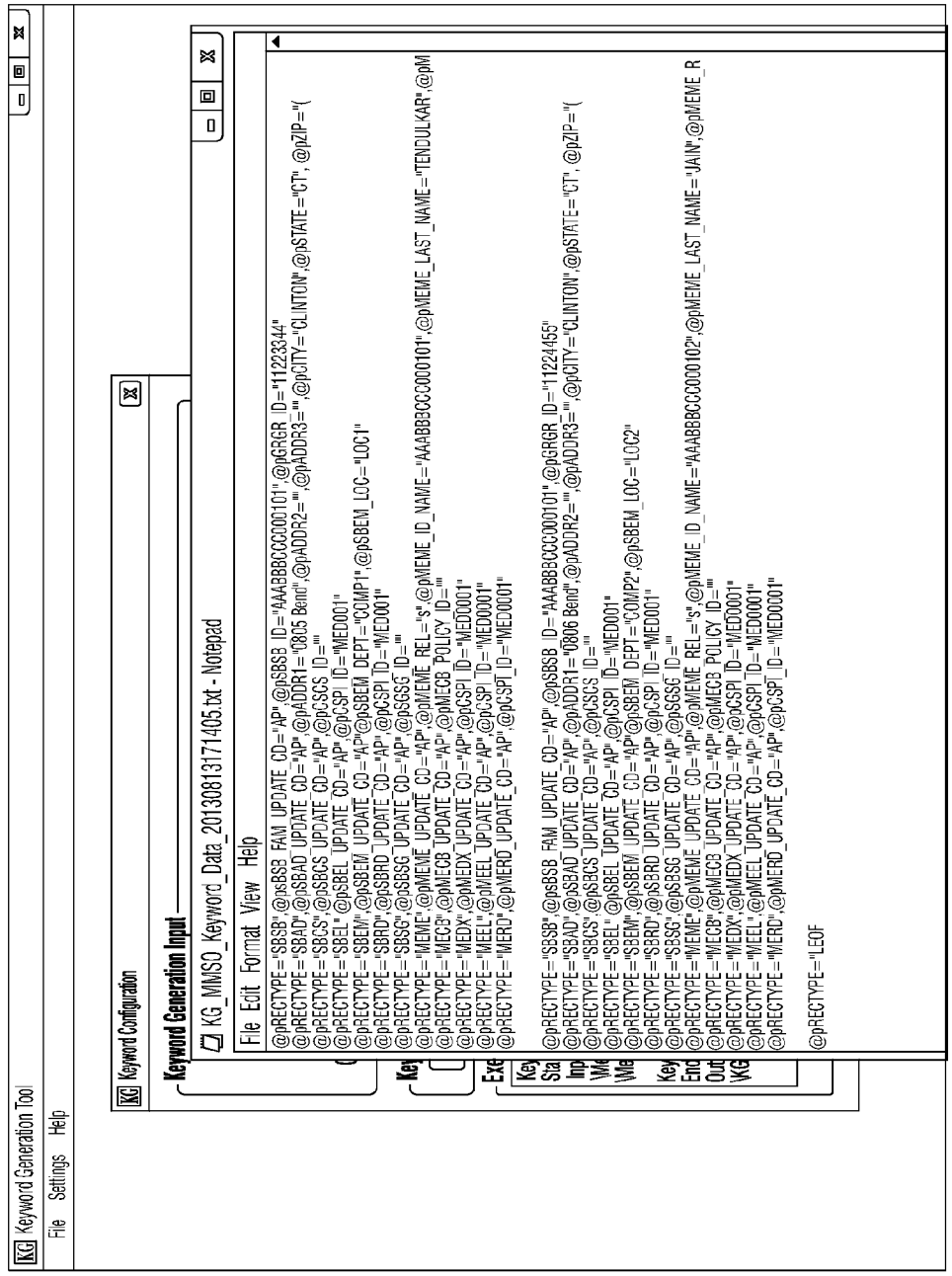

If the input file is not valid (in other words, not of a format recognized by the tool), a user may be presented with a screen as shown in FIG. 41. If the input and output locations are set, a keyword file can then be generated. An example screenshot is shown in FIG. 42 including a pop-up window 4201 stating that the keyword file was successfully generated. After generation of the keyword file, a user can preview the generated keyword file, an example screenshot of which is shown in FIG. 43.

Figure 44:
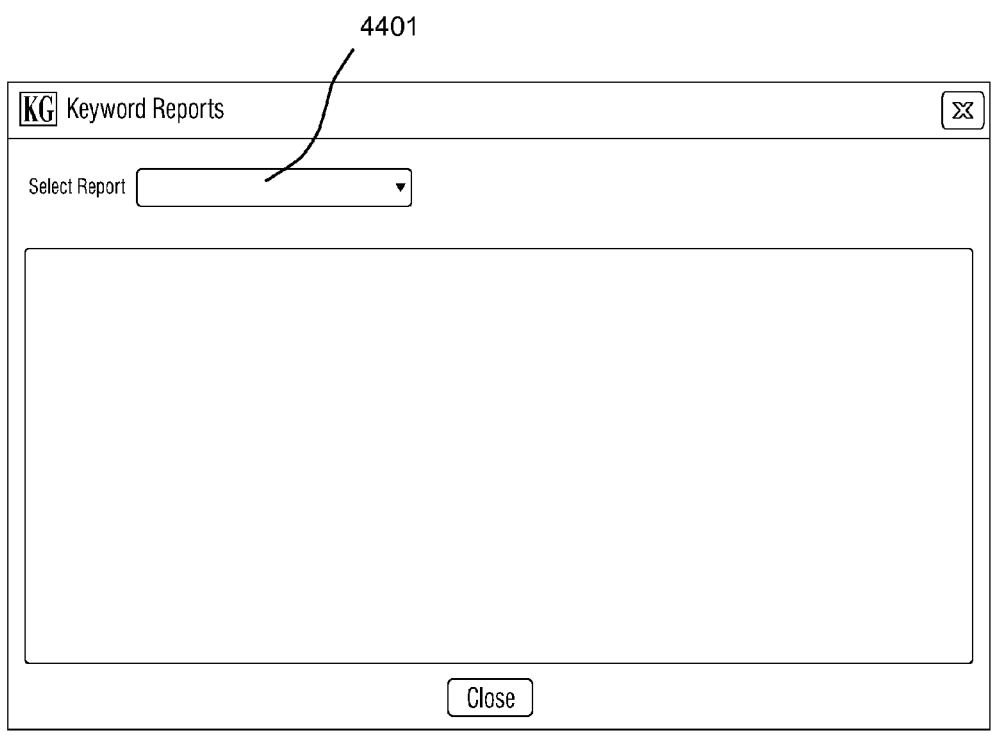
Figure 45:
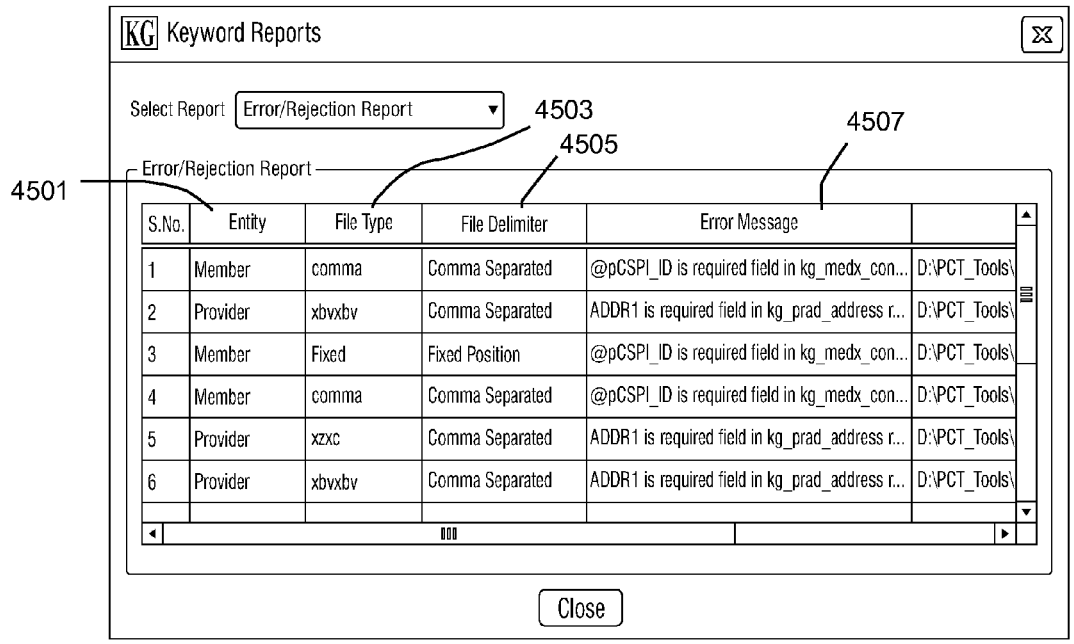
Figure 46:
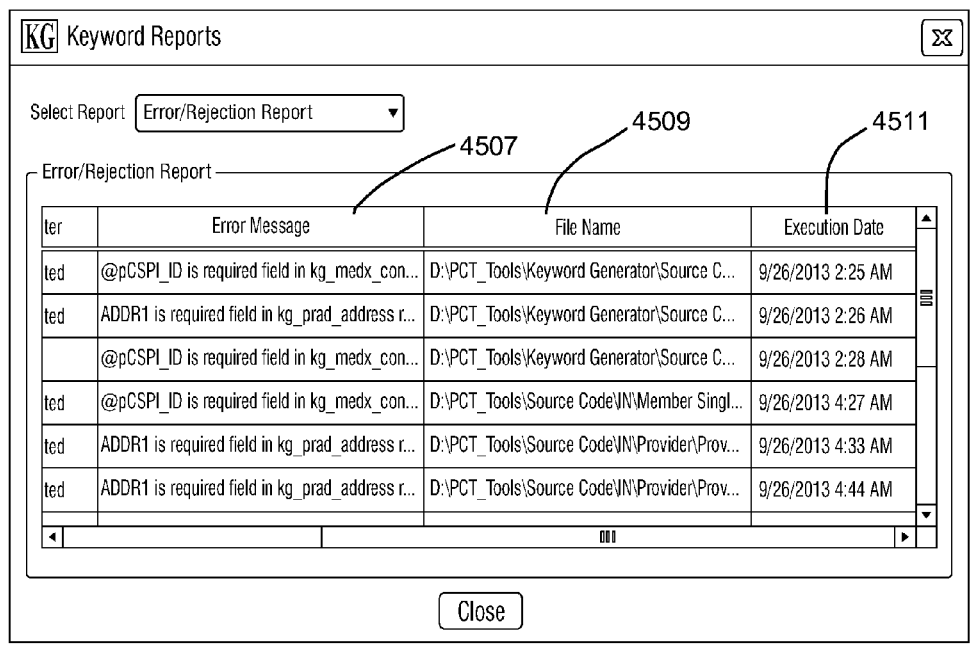

FIG. 44 is an example screenshot of the keyword generation reports home screen. Under the report drop down menu 4401, a user has the ability to choose from various reports including but not limited to an error/rejection report and fallout report. As shown in the example screenshots in FIGS. 45 and 46, the error/rejection report has been selected. As shown, the error/rejection report includes details concerning any errors found by the tool upon processing the mapping. These details include but are not limited to the an entity type 4501, file type 4503, file delimiter 4505, and any error message 4507 describing the identified error, file name 4509, and execution date 4511 as to when the error was identified.

Although the present disclosure has been described with reference to particular means, materials, and embodiments, from the foregoing description, one skilled in the art can easily ascertain the essential characteristics of the invention and various changes and modifications may be made to adapt the various uses and characteristics without departing from the spirit and scope of the invention.

What is claimed is:

1. A computerized system for generating healthcare data keyword files, the system comprising:
   a reader module on a computer configured to:
      read one or more healthcare data fields associated with a first vendor; and
      read one or more portions of healthcare data associated with the one or more data fields;
   a mapper module on a computer configured to:
      allow a first mapping of the one or more data fields to one or more keyword fields; and
   a generator module on a computer configured to:
      in accordance with the first mapping, generate one or more keywords associated with the one or more portions of healthcare data;
   wherein the reader module is further configured to read one or more healthcare data fields associated with a second vendor; and the mapper module is further configured to allow a second mapping associated with the one or more healthcare data fields associated with the second vendor;
   wherein the generator module is further configured to identify an error in the first and second mappings; and
   wherein the generator module is further configured to generate a report showing a location of the identification; wherein the report includes details concerning the error, the details include an entity type, a file type, a file delimiter, any error message, a file name, and an execution date.

2. The computerized system of claim 1, wherein the generator module is configured to generate a batch file according to at least one of the first mapping and the second mapping.

3. The computerized system of claim 1, wherein the first vendor is a first healthcare provider and the second vendor is a second healthcare provider.

4. The computerized system of claim 1, wherein the generator module is further configured to, in accordance with the second mapped one or more data fields, generate one or more keywords in accordance with the second mapped one or more data fields.

5. A computerized system for generating healthcare data keyword files, the system comprising:
   a reader module on a computer configured to:
      read one or more healthcare data fields associated with a first vendor; and
      read one or more healthcare data fields associated with a second vendor;
      read one or more portions of healthcare data associated with the one or more data fields;
   a mapper module on a computer configured to:
      allow a first mapping of the one or more first vendor data fields to one or more keyword fields;
      allow a second mapping of the one or more second vendor data fields; and
   a generator module on a computer configured to:
      in accordance with the first and second mappings, generate one or more keywords associated with the one or more portions of healthcare data,
   wherein the generated one or more keywords are compatible with at least one of a Facets Membership Maintenance Subsystem and a Facets® Provider Import Subsystem format.

6. The computerized system of claim 5, wherein the generator module is further configured to identify an error in the first and second mappings.

7. The computerized system of claim 6, wherein the error occurs when two of the one or more healthcare data fields is mapped to one keyword.

8. The computerized system of claim 7, wherein the generator module is further configured to generate a report showing a location of the identification of the error.

9. The computerized system of claim 5, wherein the reader module is further configured to validate the one or more portions of healthcare data.

10. The computerized system of claim 9, wherein the validation comprises determining whether the one or more portions of healthcare data is an appropriate format for interpretation by the generator module.

11. The computerized system of claim 10, wherein the keyword generator is configured to generate valid batch file in a format compatible with a healthcare management software.

12. A computerized system for generating healthcare data keyword files, the system comprising:
- a reader module on a computer configured to:
  - read one or more healthcare data fields associated with a first vendor; and
  - read one or more healthcare data fields associated with a second vendor;
  - read one or more portions of healthcare data associated with the one or more data fields;
- a mapper module on a computer configured to:
  - allow a first mapping of the one or more first vendor data fields to one or more keyword fields;
  - allow a second mapping of the one or more second vendor data fields; and
- a generator module on a computer configured to:
  - in accordance with the first and second mappings, generate one or more keywords associated with the one or more portions of healthcare data,
- wherein the keyword generator is configured to browse an input file, load data from the input file into a common table, analyze the loaded data via applying business rules, and load the analyzed loaded data into a child table; wherein the analyzed loaded data includes rule settings, mappings, and actual patient and provider healthcare data for generating a keyword file.

* * * * *